US011129705B2

(12) United States Patent
Li

(10) Patent No.: US 11,129,705 B2
(45) Date of Patent: Sep. 28, 2021

(54) SENSING APPARATUS, ARTIFICIAL SKIN, METHOD OF DETECTING TOUCH, AND SENSOR

(71) Applicant: BOE Technology Group Co., Ltd., Beijing (CN)

(72) Inventor: Yingyi Li, Beijing (CN)

(73) Assignee: BOE Technology Group Co., Ltd., Beijing (CN)

(*) Notice: Subject to any disclaimer, the term of this patent is extended or adjusted under 35 U.S.C. 154(b) by 212 days.

(21) Appl. No.: 16/464,230

(22) PCT Filed: Jan. 3, 2019

(86) PCT No.: PCT/CN2019/070270
§ 371 (c)(1),
(2) Date: May 24, 2019

(87) PCT Pub. No.: WO2019/205731
PCT Pub. Date: Oct. 31, 2019

(65) Prior Publication Data
US 2020/0281713 A1    Sep. 10, 2020

(30) Foreign Application Priority Data
Apr. 27, 2018 (CN) .......................... 201810391878.0

(51) Int. Cl.
*A61F 2/10* (2006.01)
*G01B 11/16* (2006.01)
*A61F 2/48* (2006.01)

(52) U.S. Cl.
CPC ............ *A61F 2/105* (2013.01); *G01B 11/167* (2013.01); *A61F 2002/482* (2013.01)

(58) Field of Classification Search
CPC ................................ G06F 3/042; G06F 3/045
See application file for complete search history.

(56) References Cited

U.S. PATENT DOCUMENTS

2010/0078636 A1    4/2010  Zachariasse
2010/0277431 A1*  11/2010  Klinghult ............. G06F 3/0412
345/174

(Continued)

FOREIGN PATENT DOCUMENTS

CN    101617319 A    12/2009
CN    105183241 A    12/2015

(Continued)

OTHER PUBLICATIONS

International Search Report & Written Opinion dated Apr. 8, 2019, regarding PCT/CN2019/070270.

(Continued)

*Primary Examiner* — Yashita Sharma
(74) *Attorney, Agent, or Firm* — Intellectual Valley Law, P.C.

(57) ABSTRACT

A sensing apparatus includes a base substrate; a plurality of sensing units on the base substrate, a respective one of the plurality of sensing units including a first component configured to emit light and a second component configured to detect light; and an elastic layer on a side of the plurality of sensing units distal to the base substrate and configured to undergo a deformation upon a touch, at least a portion of light emitted from the first component being reflected by a surface of the elastic layer. The second component is configured to detect light reflected by the surface of the elastic layer and output a sensing signal, an intensity of which being correlated to a degree of the deformation of the elastic layer at a local position.

16 Claims, 12 Drawing Sheets

(56) References Cited

U.S. PATENT DOCUMENTS

2015/0035799 A1* 2/2015 Lin ...................... G06F 3/0421
                                                      345/175
2018/0020934 A1    1/2018 Park et al.

FOREIGN PATENT DOCUMENTS

| CN | 106648264 A | 5/2017 |
| CN | 107135290 A | 9/2017 |
| CN | 107421681 A | 12/2017 |
| JP | 4544632 B2 | 9/2010 |
| JP | 2017181442 A | 10/2017 |

OTHER PUBLICATIONS

First Office Action in the Chinese Patent Application No. 201810391878.0, dated May 30, 2019; English translation attached.

* cited by examiner

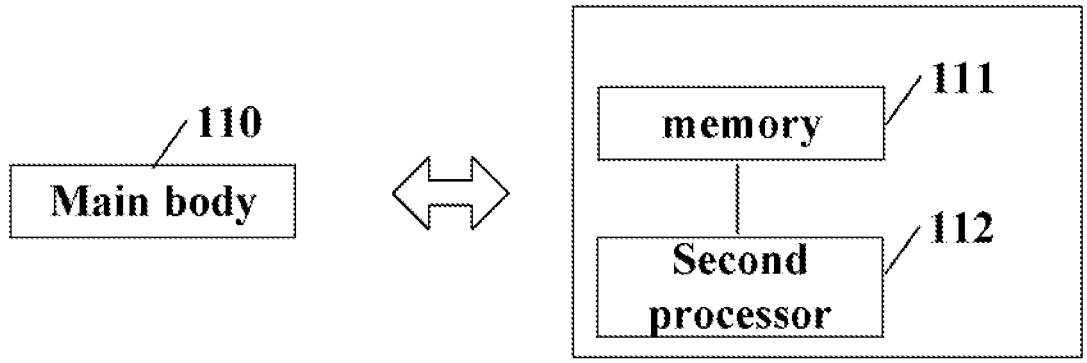

FIG. 10

| forming a plurality of sensing units on a base substrate, each of the plurality of sensing units formed to include a first component configured to emit light and a second component configured to detect light |
|---|
| forming an elastic layer on a side of the plurality of sensing units distal to the base substrate and configured to undergo a deformation upon a touch, at least a portion of light emitted from the first component being reflected by a surface of the elastic layer, the second component being formed to detect light reflected by the surface of the elastic layer and output a sensing signal, an intensity of which being correlated to a degree of the deformation of the elastic layer at a local position |

FIG. 11

| forming a memory configured to store a plurality of reference sensing signals corresponding to different degrees of deformation |
|---|
| forming a second processor configured to receive the sensing signal from the second component of each of the plurality of sensing units, compare the sensing signal from the second component of each of the plurality of sensing units with the plurality of reference sensing signals, and determine the degree of the deformation of the elastic layer at each local position based on comparison between the sensing signal from the second component of each of the plurality of sensing units and the plurality of reference sensing signals |

FIG. 12 outputting a first sensing signal from the second component of each of the plurality of sensing units upon receiving light reflected by a surface of the elastic layer by the second component

↓ determining a degree of the deformation of the elastic layer at each local position based on the sensing signal from the second component

FIG. 13 outputting a first sensing signal from the second component of each of the plurality of sensing units upon receiving light reflected by a surface of the elastic layer by the second component

↓ based on a plurality of reference sensing signals corresponding to different degrees of deformation stored in a memory, comparing the sensing signal from the second component of each of the plurality of sensing units with the plurality of reference sensing signals

↓ determining the degree of the deformation of the elastic layer at each local position based on comparison between the sensing signal from the second component of each of the plurality of sensing units and the plurality of reference sensing signals

FIG. 14

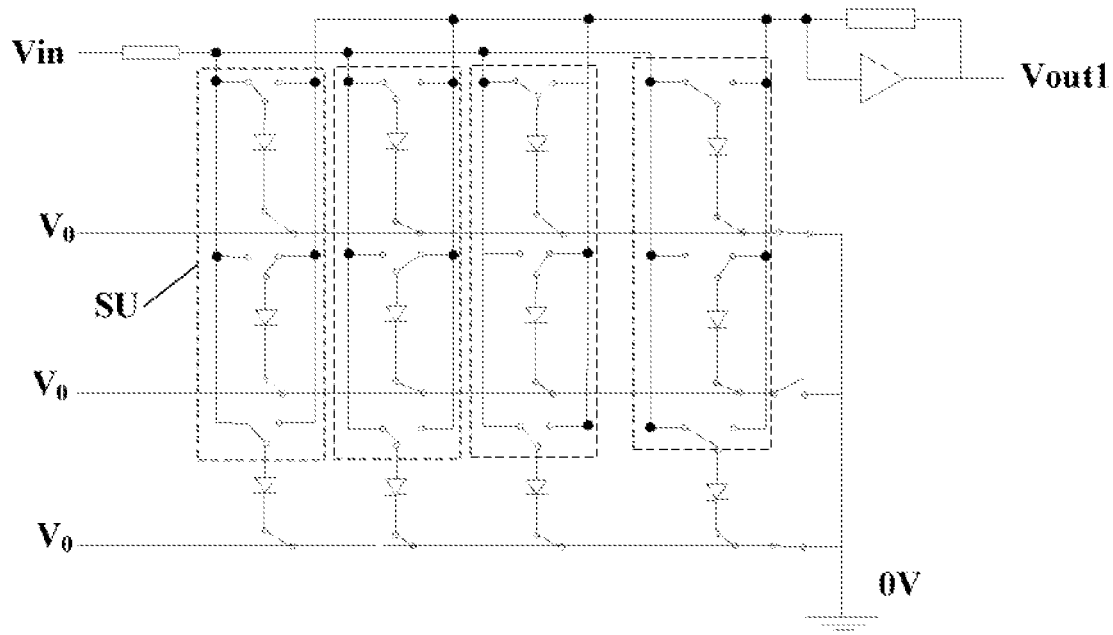

FIG. 15 sequentially inputting a first control signal to first selector switches at a given time interval, sequentially inputting a second control signal to second selector switches at a given time interval, sequentially inputting a third control signal to third selector switches at a given time interval, sequentially inputting a fourth control signal to fourth selector switches at a given time interval

↓ detecting in real time a first output voltage from the first output voltage signal line using a voltage detector when the first control signal and the second control signal are inputted

↓ counting a time duration during which the first output voltage undergoes a change exceeding a threshold value

↓ comparing the time duration with time points at which the plurality of sensing units respectively receiving the first control signal to determine a sensing unit subject to touch

↓ comparing a change in a voltage level of the first output voltage during the time duration with a plurality of reference voltage levels to determine a touch pressure

FIG. 21 in a first mode, sequentially inputting a first control signal to first selector switches at a given time interval, sequentially inputting a second control signal to second selector switches at a given time interval, sequentially inputting a third control signal to third selector switches at a given time interval, sequentially inputting a fourth control signal to fourth selector switches at a given time interval

↓ detecting in real time a first output voltage from the first output voltage signal line using a voltage detector when the first control signal, the second control signal, the third control signal, and the fourth control signal are inputted

↓ in a second mode, sequentially inputting a fifth control signal to first selector switches at a given time interval, sequentially inputting a sixth control signal to second selector switches at a given time interval, sequentially inputting a seventh control signal to third selector switches at a given time interval, sequentially inputting a eighth control signal to fourth selector switches at a given time interval

↓ detecting in real time a second output voltage from the first output voltage signal line using the voltage detector when the fifth control signal, the sixth control signal, the seventh control signal, and the eighth control signal are inputted

↓ counting a time duration during which the first output voltage and the second output voltage respectively undergo a change exceeding a threshold value

↓ comparing the time duration with time points at which the plurality of sensing units respectively receiving control signals to determine a sensing unit subject to touch

↓ comparing changes in voltage levels of the first output voltage and the second output voltage during the time duration with a plurality of first reference voltage levels and a plurality of second reference voltage levels respectively to determine a touch pressure

FIG. 22

SENSING APPARATUS, ARTIFICIAL SKIN, METHOD OF DETECTING TOUCH, AND SENSOR

CROSS-REFERENCE TO RELATED APPLICATION

This application is a national stage application under 35 U.S.C. § 371 of International Application No. PCT/CN2019/070270, filed Jan. 3, 2019, which claims priority to Chinese Patent Application No. 201810391878.0, filed Apr. 27, 2018, the contents of which are incorporated by reference in the entirety.

TECHNICAL FIELD

The present invention relates to touch sensing technology, more particularly, to a sensing apparatus, an artificial skin, a method of detecting a touch, and a sensor.

BACKGROUND

Artificial skin has been developed in recent years, and has found applications in many fields. For example, prosthetic limbs can be covered with artificial skin to provide the user with sensing functions. Robotic limbs can be covered with artificial skin to allow better control for performing various functions.

SUMMARY

In one aspect, the present invention provides a sensing apparatus, comprising a base substrate; a plurality of sensing units on the base substrate, a respective one of the plurality of sensing units comprising a first component configured to emit light and a second component configured to detect light; and an elastic layer on a side of the plurality of sensing units distal to the base substrate and configured to undergo a deformation upon a touch, at least a portion of light emitted from the first component being reflected by a surface of the elastic layer; wherein the second component is configured to detect light reflected by the surface of the elastic layer and output a sensing signal, an intensity of which being correlated to a degree of the deformation of the elastic layer at a local position.

Optionally, the sensing apparatus further comprises a reflective layer on a side of the elastic layer distal to the base substrate, and configured to block light emitted from the first component from emitting out of the elastic layer.

Optionally, the sensing apparatus further comprises a processor configured to receive the sensing signal from the second component of the respective one of the plurality of sensing units, and determine the degree of the deformation of the elastic layer at each local position based on the sensing signal from the second component of the respective one of the plurality of sensing units.

Optionally, the sensing apparatus further comprises a memory configured to store a plurality of reference sensing signals corresponding to different degrees of deformation; and a processor configured to receive the sensing signal from the second component of the respective one of the plurality of sensing units, compare the sensing signal from the second component of the respective one of the plurality of sensing units with the plurality of reference sensing signals, and determine the degree of the deformation of the elastic layer at each local position based on comparison between the sensing signal from the second component of the respective one of the plurality of sensing units and the plurality of reference sensing signals.

Optionally, the sensing apparatus further comprises an input voltage signal line; a first output voltage signal line; a reference voltage signal line; a ground voltage signal line; a first selector switch configured to selectively couple a first terminal of the first component to one of the input voltage signal line or the first output voltage signal line; a second selector switch configured to selectively couple a second terminal of the first component to one of the reference voltage signal line or the ground voltage signal line; a third selector switch configured to selectively couple a first terminal of the second component to one of the input voltage signal line or the first output voltage signal line; and a fourth selector switch configured to selectively couple a second terminal of the second component to one of the reference voltage signal line or the ground voltage signal line.

Optionally, the first component is configured to emit light when a voltage level at the first terminal of the first component is higher than a voltage level at the second terminal of the first component to generate a current flowing from the first terminal of the first component to the second terminal of the first component; and the second component is configured to detect light when a voltage level at the second terminal of the second component is higher than a voltage level at the first terminal of the second component to generate a photocurrent flowing from the second terminal of the second component to the first terminal of the second component.

Optionally, the first component is configured to detect light when a voltage level at the second terminal of the first component is higher than a voltage level at the first terminal of the first component to generate a photocurrent flowing from the second terminal of the first component to the first terminal of the first component; and the second component is configured to emit light when a voltage level at the first terminal of the second component is higher than a voltage level at the second terminal of the second component to generate a current flowing from the first terminal of the second component to the second terminal of the second component.

Optionally, the respective one of the plurality of sensing units further comprises a third component; wherein the sensing apparatus further comprises a second output voltage signal line; a fifth selector switch configured to selectively couple a first terminal of the third component to one of the input voltage signal line or the second output voltage signal line; and a sixth selector switch configured to selectively couple a second terminal of the third component to one of the reference voltage signal line or the ground voltage signal line, wherein the third component is configured to detect light when a voltage level at the second terminal of the third component is higher than a voltage level at the first terminal of the third component to generate a photocurrent flowing from the second terminal of the third component to the first terminal of the third component.

Optionally, a total number of components in the respective one of the plurality of sensing units configured to emit light is one and a total number of components in the respective one of the plurality of sensing units configured to detect light is two.

Optionally, the first component is a light emitting diode and the second component is a photodiode.

Optionally, the first component is a photodiode and the second component is a photodiode.

Optionally, the elastic layer comprises an elastic resin material.

In another aspect, the present invention provides an artificial skin, comprising the sensing apparatus described herein or fabricated by a method described herein, wherein the base substrate is a flexible base substrate.

In another aspect, the present invention provides a method of detecting a touch, comprising emitting light from a first component of a respective one of a plurality of sensing units; reflecting at least a portion of light emitted from the first component by a surface of an elastic layer; detecting light reflected by the surface of the elastic layer by a second component of the respective one of the plurality of sensing units; and outputting a first sensing signal from the second component of the respective one of the plurality of sensing units; wherein an intensity of the first sensing signal is correlated to a degree of the deformation of the elastic layer at a local position.

Optionally, the method further comprises sequentially selectively coupling first terminals of first components of the plurality of sensing units to an input voltage signal line at a given time interval; sequentially selectively coupling second terminals of first components of the plurality of sensing units to a ground voltage signal line at a given time interval; sequentially selectively coupling first terminals of second components of the plurality of sensing units to a first output voltage signal line at a given time interval; sequentially selectively coupling second terminals of second components of the plurality of sensing units to a reference voltage signal line at a given time interval; and detecting a first output voltage from the first output voltage signal line thereby determining a touch position and a touch pressure.

Optionally, the method further comprises emitting light from the second component of the respective one of a plurality of sensing units; reflecting at least a portion of light emitted from the second component by the surface of the elastic layer; detecting light reflected by the surface of the elastic layer by the first component of the respective one of the plurality of sensing units; and outputting a second sensing signal from the first component of the respective one of the plurality of sensing units; wherein the intensity of the second sensing signal is correlated to a degree of the deformation of the elastic layer at a local position.

Optionally, the method further comprises sequentially selectively coupling first terminals of second components of the plurality of sensing units to an input voltage signal line at a given time interval, sequentially selectively coupling second terminals of second components of the plurality of sensing units to a ground voltage signal line at a given time interval; sequentially selectively coupling first terminals of first components of the plurality of sensing units to a first output voltage signal line at a given time interval; sequentially selectively coupling second terminals of first components of the plurality of sensing units to a reference voltage signal line at a given time interval; and detecting a second output voltage from the first output voltage signal line thereby determining a touch position and a touch pressure.

Optionally, the method further comprises further detecting light reflected by the surface of the elastic layer by a third component of the respective one of the plurality of sensing units; and outputting a third sensing signal from the third component of the respective one of the plurality of sensing units; wherein an intensity of the third sensing signal is correlated to a degree of the deformation of the elastic layer at a local position.

Optionally, the method further comprises sequentially selectively coupling first terminals of first components of the plurality of sensing units to an input voltage signal line at a given time interval; sequentially selectively coupling second terminals of first components of the plurality of sensing units to a ground voltage signal line at a given time interval; sequentially selectively coupling first terminals of second components of the plurality of sensing units to a first output voltage signal line at a given time interval; sequentially selectively coupling second terminals of second components of the plurality of sensing units to a reference voltage signal line at a given time interval; sequentially selectively coupling first terminals of third components of the plurality of sensing units to a second output voltage signal line at a given time interval; sequentially selectively coupling second terminals of third components of the plurality of sensing units to the reference voltage signal line at a given time interval; and detecting a first output voltage from the first output voltage signal line and a second output voltage from the second output voltage signal line, thereby determining a touch position and a touch pressure.

In another aspect, the present invention provides a method of fabricating a sensing apparatus, comprising forming a plurality of sensing units on a base substrate, the respective one of the plurality of sensing units formed to comprise a first component configured to emit light and a second component configured to detect light; and forming an elastic layer on a side of the plurality of sensing units distal to the base substrate and configured to undergo a deformation upon a touch, at least a portion of light emitted from the first component being reflected by a surface of the elastic layer; wherein the second component is formed to detect light reflected by the surface of the elastic layer and output a sensing signal, an intensity of which being correlated to a degree of the deformation of the elastic layer at a local position.

BRIEF DESCRIPTION OF THE FIGURES

The following drawings are merely examples for illustrative purposes according to various disclosed embodiments and are not intended to limit the scope of the present invention.

FIG. 10 is a diagram illustrating the structure of a sensing apparatus in some embodiments according to the present disclosure.

FIG. 11 is a flow chart illustrating a method of fabricating a sensing apparatus in some embodiments according to the present disclosure.

FIG. 12 is a flow chart illustrating a method of fabricating a sensing apparatus in some embodiments according to the present disclosure.

FIG. 13 is a flow chart illustrating a method of detecting a touch in some embodiments according to the present disclosure.

FIG. 14 is a flow chart illustrating a method of detecting a touch in some embodiments according to the present disclosure.

FIG. 15 is a circuit diagram of a sensing circuit in some embodiments according to the present disclosure.

FIG. 21 is a flow chart illustrating a method of detecting a touch in some embodiments according to the present disclosure.

FIG. 22 is a flow chart illustrating a method of detecting a touch in some embodiments according to the present disclosure.

DETAILED DESCRIPTION

The disclosure will now be described more specifically with reference to the following embodiments. It is to be noted that the following descriptions of some embodiments are presented herein for purpose of illustration and description only. It is not intended to be exhaustive or to be limited to the precise form disclosed.

Piezoelectric pressure sensor have been developed and commercialized as sensors for detecting touch pressure. Typically, these piezoelectric pressure sensors have a relatively low resolution, and can only detect pressure applied from a certain direction. In order to have a certain accuracy, the piezoelectric pressure sensor unit has to be made relatively large. Thus, the piezoelectric pressure sensors are not suitable for pressure detection with a high accuracy requirement, particularly in miniaturized instruments. Moreover, the fabricating process of the piezoelectric pressure sensors is costly and complicated, placing a high demand on process precision.

Accordingly, the present disclosure provides, inter cilia, a sensing apparatus, an artificial skin, a method of detecting a touch, and a sensor that substantially obviate one or more of the problems due to limitations and disadvantages of the related art. In one aspect, the present disclosure provides a sensing apparatus. In some embodiments, the sensing apparatus includes a base substrate; a plurality of sensing units on the base substrate, a respective one of the plurality of sensing units including a first component configured to emit light and a second component configured to detect light; and an elastic layer on a side of the plurality of sensing units distal to the base substrate and configured to undergo a deformation upon a touch, at least a portion of light emitted from the first component being reflected by a surface of the elastic layer. Optionally, the second component is configured to detect light reflected by the surface of the elastic layer and output a sensing signal. Optionally, an intensity of the sensing signal output from the second component is correlated to a degree of the deformation of the elastic layer at a local position.

Figure 1:
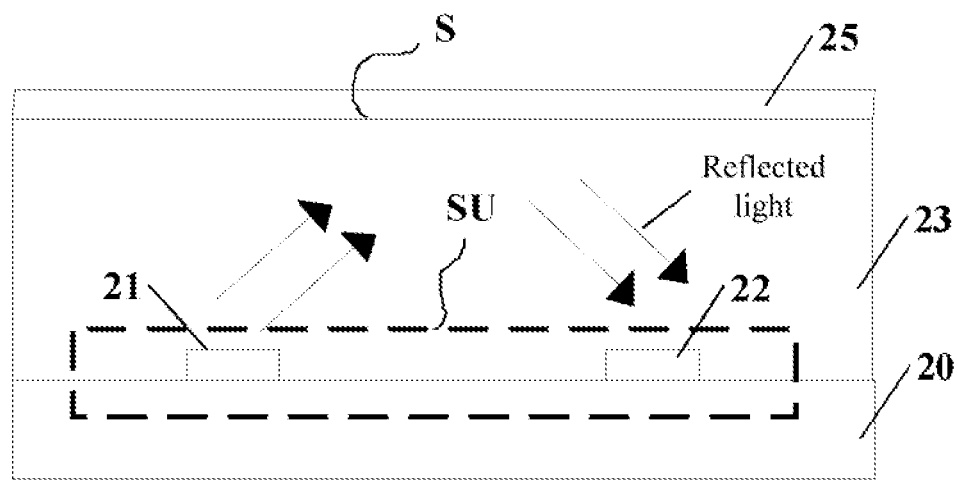
FIG. 1 is a diagram illustrating the structure of a sensing apparatus in some embodiments according to the present disclosure.

FIG. 1 is a diagram illustrating the structure of a sensing apparatus in some embodiments according to the present disclosure. Referring to FIG. 1, the sensing apparatus in some embodiments includes a base substrate 20 and a plurality of sensing unit SU on the base substrate 20. A respective one of the plurality of sensing unit SU includes a first component 21 configured to emit light and a second component 22 configured to detect light. The sensing apparatus in some embodiments further includes an elastic layer 23 on a side of the plurality of sensing units SU distal to the base substrate 20 and configured to undergo a deformation upon a touch, at least a portion of light emitted from the first component 21 being reflected by a surface S of the elastic layer 23. Optionally, the elastic layer 23 at least partially covers the plurality of sensing units SU.

Figure 2:
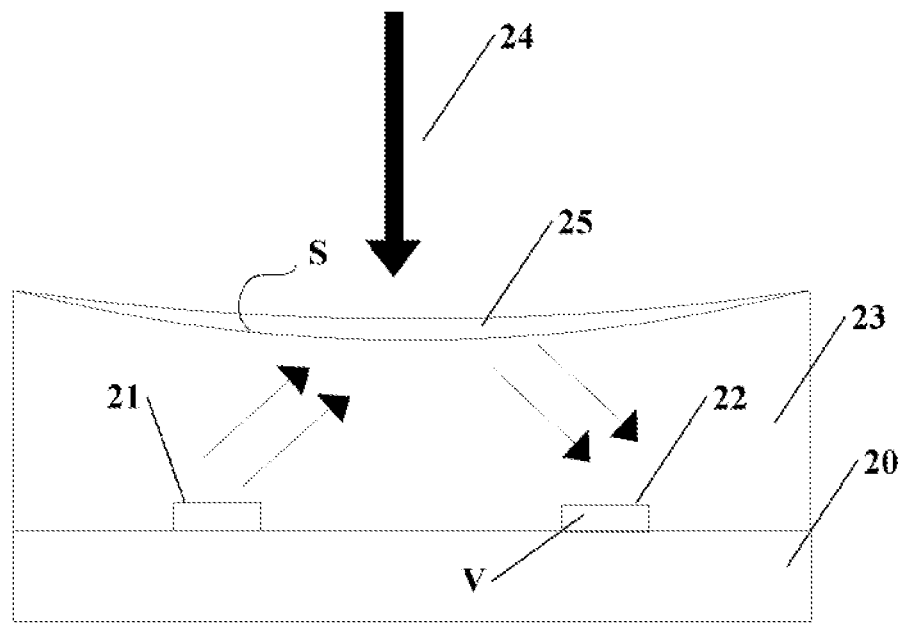
FIG. 2 is a diagram illustrating the structure of a sensing apparatus during a touch event in some embodiments according to the present disclosure.

FIG. 2 is a diagram illustrating the structure of a sensing apparatus during a touch event in some embodiments according to the present disclosure. Referring to FIG. 2, the sensing apparatus is subject to a touch, e.g., a force 24 is applied to the surface S of the elastic, layer 23. Upon the application of the force 24, the elastic layer 23 undergoes a deformation at a local position as shown in FIG. 2. Optionally, the second component 22 is configured to detect light reflected by the surface S of the elastic layer 23 and output a sensing signal (e.g., a voltage signal v as shown in FIG. 2). Optionally, an intensity of the sensing signal output from the second component 22 is correlated to a degree of the deformation of the elastic layer 23 at a local position.

Various appropriate materials may be used for making the base substrate 20. Examples of appropriate materials for making the base substrate 20 include glass, silicon, quartz, and flexible materials such as polyimide, polycarbonate, polyethersulfone, polyethylene terephthalate, polyethylene naphthalate, polyarylate, and fiber-reinforced plastic. Optionally, the base substrate 20 is made of a flexible material. A flexible base substrate is particularly suitable in applications such as making artificial skins having the sensing apparatus integrated therein. The artificial skin typically requires it sufficiently flexible for attaching on non-flat surface.

Various appropriate materials may be used for making the elastic layer 23. Examples of appropriate materials for making the elastic layer 23 include polyimides, polysilicones, polysiloxanes, polyepoxides, silicone-based polymers (e.g., polydimethylsiloxane-based materials such as polydimethylsiloxane, hexamethyldisiloxane, and polyphenylmethylsiloxane), polyurethane-based materials (such as polyurethane, polyurethane acrylate, polyether urethane, and polycarbonate-polyurethane elastomers), polyvinylfluoride, polyvinylchloride, acrylate polymer, acrylate terpolymer, rubbers (e.g., chloroprene rubber, acryl-based rubber, and nitrile rubber), polyvinylpyrrolidone, polyvinyl alcohol, polymethyl methacrylate, cellulose acetate, cellulose acetate butyrate, cellulose acetate propionate, polymethyl acrylate, polyvinyl acetate, polyacrylonitrile, polyfurfuryl alcohol, polystyrene, polyethylene oxide, polypropylene oxide, polycarbonate, polyvinyl chloride, polycaprolactone, and any combination thereof. Optionally, the elastic layer 23 is made of an elastic resin material.

Optionally, the elastic layer 23 has a Young's modulus in a range of approximately 0.001 GPa to approximately 1.5 GPa, e.g., approximately 0.001 GPa to approximately 0.05 GPa, approximately 0.05 GPa to approximately 0.1 GPa, approximately 0.1 GPa to approximately 0.2 GPa, approximately 0.2 GPa to approximately 0.3 GPa, approximately 0.3 GPa to approximately 0.4 GPa, and approximately 0.4 GPa to approximately 0.5 GPa, approximately 0.5 GPa to approximately 1.0 GPa and approximately 1.0 GPa to approximately 1.5 GPa.

In some embodiments, the sensing apparatus includes a simile one sensing unit (which includes a first component 21 and a second component 22 as discussed above).

Figure 8:
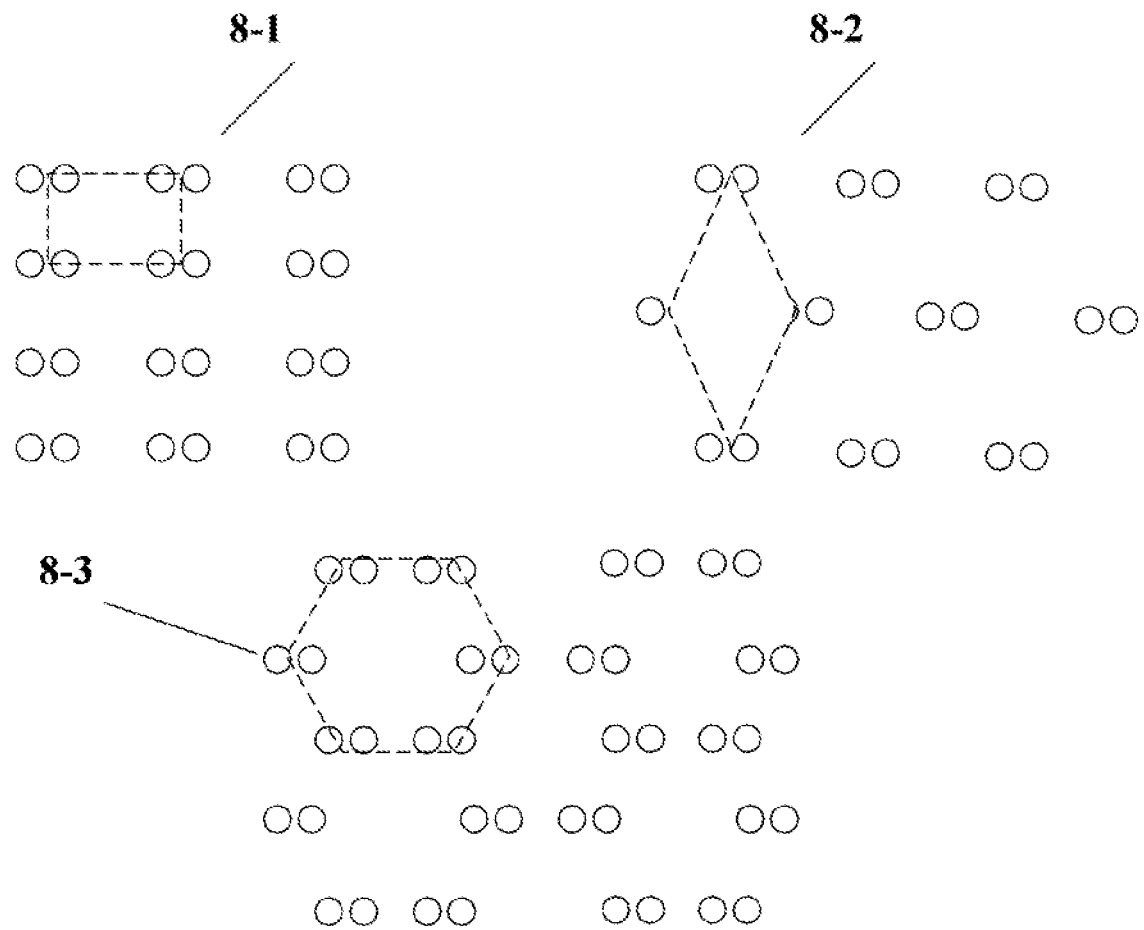
FIG. 8 illustrates various arrangements of sensor units in a sensing apparatus in some embodiments according to the present disclosure.

In some embodiments, the sensing apparatus includes the plurality of sensing unit SU arranged in a form of an array. FIG. 8 illustrates various arrangements of sensor units in a sensing apparatus in some embodiments according to the present disclosure. As shown in FIG. 8, the plurality of sensing unit SU may be arranged in various appropriate forms of arrays, such as a rectangular array (8-1), a rhombohedral array (8-2), and a hexagonal array (8-3).

Referring, to FIG. 1 and FIG. 2, the sensing apparatus in some embodiments further includes a reflective layer 25 on a side of the elastic layer 23 distal to the base substrate 20. The reflective layer 25 is configured to block light emitted from the first component 21 from emitting out of the elastic layer 22. The reflective layer 25 may be a reflective film e.g., a reflective metal film) disposed on a side of the elastic layer 23 distal to the base substrate 20.

Various appropriate materials and various appropriate fabricating methods may be used to make the reflective layer 25. For example, a reflective material may be deposited by a plasma-enhanced chemical vapor deposition (PECVD) process. Examples of appropriate reflective materials for making the reflective layer 25 include, but are not limited to, silver, aluminum, and titanium. By having a reflective layer 25, diffused reflection of light emitted from the first component 21 can be avoided as much as possible, the light reflected by the reflective layer 25 can be limited to a same sensing unit to the extent possible. By having the reflective layer 25, interference among adjacent sensing units can be avoided as much as possible, enhancing detection accuracy of a respective one of the plurality of sensing units SU.

In some embodiments, the reflective layer 25 and the elastic layer 23 are integrated together. For example, the elastic layer 23 may be a reflective elastic layer made of a reflective and elastic material.

In some embodiments, the intensity of the sensing signal output from the second component 22 can be described or expressed using a detectable value or a value that directly reflecting the intensity of light received by the second component 22. Further, the value describing the intensity of light received by the second component 22 reflects the degree of the deformation of the elastic layer at the local position. In one example, the value is zero, which denotes that the second component 22 does not receive any detectable light from the first component 21. Examples of detectable values of the intensity of the sensing signal include, but are not limited to, an output voltage signal, an output current signal, or other appropriate signals correlated to the intensity of light received by the second component 22.

Upon applications of different forces to a surface of the sensing apparatus, the elastic layer 23 undergoes deformation of different degrees, and degrees of interference on the light transmission from the first component 21 to the second component 22 are different, and the second component 22 outputs different sensing signals. Referring to FIG. 1 and FIG. 2 again, at least a portion of light emitted from the first component 21 is reflected by the surface S of the elastic layer 23 on a side distal to the base substrate 20, and the second component 22 detects the at least the portion of light reflected by the surface S of the elastic layer 23. The second component 22, based on the intensity of light received, generates a voltage signal in its equivalent circuit. Based on the magnitude of the voltage signal, the sensing apparatus determines the intensity of light received by the second component, and in turn determines whether a force 24 is applied to the sensing apparatus at the local position, and if so, the position and magnitude of the force being applied.

Figure 4:
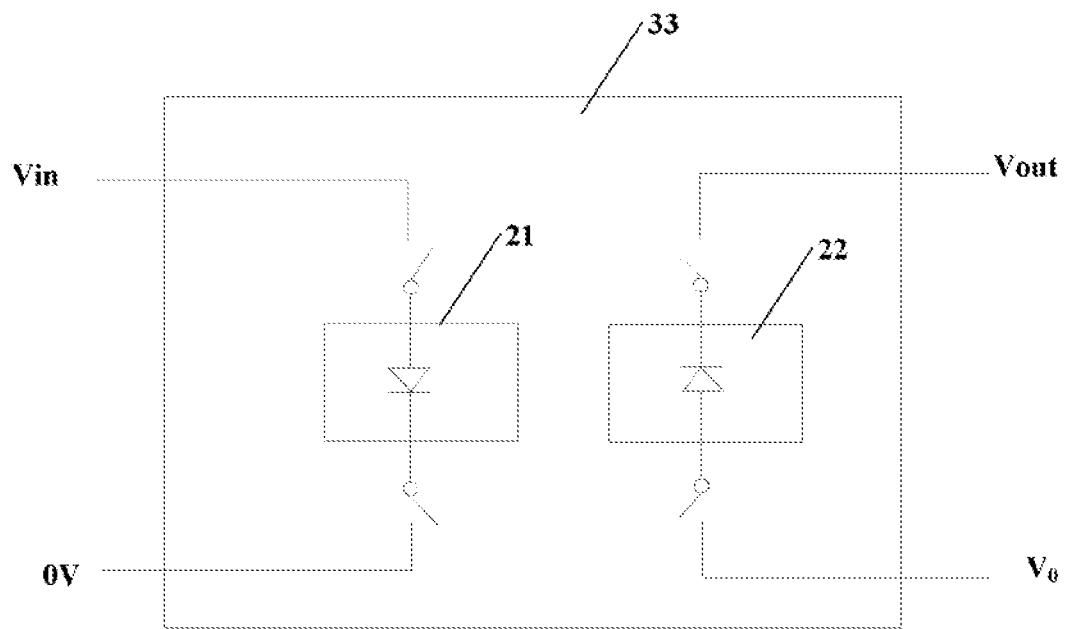
FIG. 4 is a circuit diagram of a sensing circuit in some embodiments according to the present disclosure.

In some embodiments, the sensing apparatus further includes a sensing circuit. FIG. 4 is a circuit diagram of a sensing circuit in some embodiments according to the present disclosure. Referring to FIG. 4, the sensing circuit in some embodiments includes a light emitting circuit, in which a first terminal of the first component 21 is provided with an input voltage signal Vin, and a second terminal of the first component 21 is connected to a ground voltage 0V. The sensing circuit in some embodiments further includes a light detecting circuit in which a first terminal of the second component 22 outputs a sensing signal Vout, and a second terminal of the second component 22 is connected to a reference voltage signal V0.

Various appropriate light emitting elements may be used as the first component 21 in the present sensing apparatus. Examples of appropriate light emitting elements include a light emitting diode such as an organic light emitting diode, a quantum dots light emitting diode, and a micro light emitting diode. Examples of light emitting elements further induct a photodiode.

Various appropriate light detecting elements may be used as the second component 2 in the present sensing apparatus. Examples of appropriate light detecting elements include various photosensors. Optionally, the second component 22 includes a photodiode.

Optionally, the first component 21 is configured to emit substantially collimated light. Optionally, the first component 21 is configured to emit diffused light. Optionally, a respective one of the plurality of sensing units SU includes a single one of the first component 21. Optionally, a respective one of the plurality of sensing units SU includes multiple ones of the first component 21. Optionally, a respective one of the plurality of sensing units SU includes a single one of the second component 22. Optionally, a respective one of the plurality of sensing units SU includes multiple ones of the second component 22. The components (e.g., the first component 21 and the second component 22) in the plurality of sensing units SU are spaced apart from each other such that in the respective one of the plurality of sensing units SU, the second component 22 receives at least a portion of light emitted from the first component 21 and reflected by the surface S of the elastic layer 23 when the elastic layer 23 is substantially undeformed, and light received by the second component 22 has a different intensity when the elastic layer 23 undergoes a deformation to change the reflective angle of the surface S.

In some embodiments, the second component 22 is configured not to receive any light emitted from the first component 21 and reflected by the surface S of the elastic layer 23 when the elastic layer 23 is substantially undeformed. For example, the first component 21 and the second component 22 in a respective one of the plurality of sensing units SU are spaced apart from each other by a distance such that no light emitted from the first component 21 and reflected by the surface S of the elastic layer 23 reaches the second component 22. Optionally, the second component 22 is configured to receive at least a portion of light emitted from the first component 21 and reflected by the surface S of the elastic layer 23 when the elastic layer 23 undergoes a deformation.

In some embodiments, the sensing apparatus is configured to detect whether a pressure applied to the elastic layer 23 by the force 24 exceeds a threshold. Optionally, the sensing apparatus is configured to be an alarm. Optionally, multiple sensing units of the plurality of sensing units SU of the sensing apparatus are configured to respectively detect pressures applied to the elastic layer 23 exceeding different threshold values. Optionally, the sensing apparatus can detect an approximate range of pressure applied to the sensing apparatus based on the output (or absence thereof) of the multiple sensing units. Optionally, the sensing apparatus is configured to be a multi-phase alarm.

Various other implementations may be practiced using the present sensing apparatus. Examples of applications of the present sensing apparatus include an artificial skin, sensing apparatus in a precision instrument, biomedical diagnosis, and so on. The sensing apparatus may be miniaturized to suit the applications. Optionally, the first component 21 includes a photodiode and the second component 22 includes a photodiode.

Figure 6:
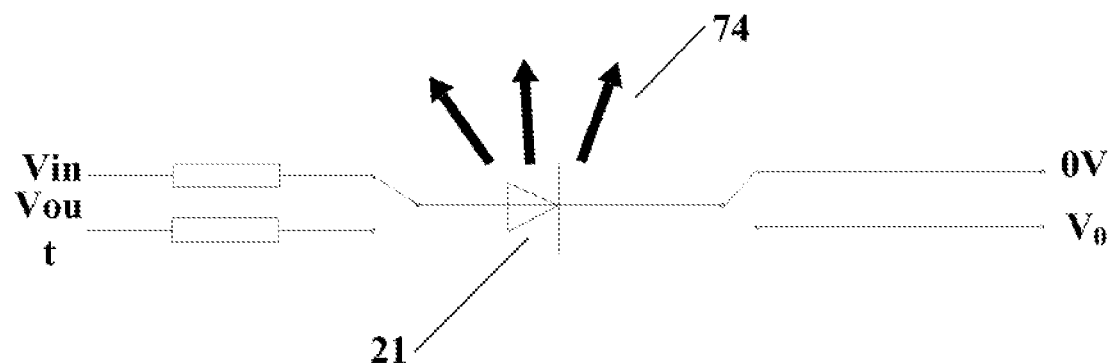
FIG. 6 is a circuit diagram of a first component of a sensing circuit in some embodiments according to the present disclosure.
Figure 7:
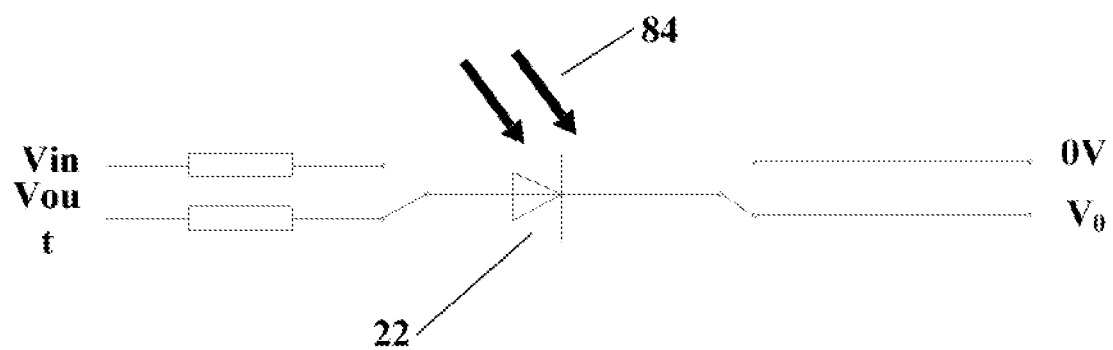
FIG. 7 is a circuit diagram of a second component of a sensing circuit in some embodiments according to the present disclosure.

FIG. 6 is a circuit diagram of a first component of a sensing circuit in some embodiments according to the present disclosure. FIG. 7 is a circuit diagram of a second component of a sensing circuit in some embodiments according to the present disclosure. Referring to FIG. 6 and FIG. 7, in some embodiments, the first component 21 is a photodiode and the second component 22 is also a photodiode. The photodiode includes a P/N junction which makes it highly sensitive to light intensity change. The photodiode has unidirectional conductivity. When the photodiode is used as a first component 21, an input voltage signal Vin is provided to the first terminal of the photodiode to generate a forward voltage from the first terminal to the second terminal in the equivalent circuit, the photodiode emits light 74. The photodiode has a small saturated reverse drain voltage, e.g., a dark voltage, when the photodiode is not exposed to light, at which time the photodiode is turned off. When the photodiode is exposed to light 84 (as shown in FIG. 7), the saturated reverse drain voltage increases, forming a photovoltage that varies with the intensity of the incident light 84. When light irradiates on the P/N junction, electron-hole pairs are generated in the P/N junction, increasing a density of some carriers. The carriers drift under the reverse voltage, increasing the reverse voltage. One terminal of the photodiode (as the second component 22) is provided with a reference voltage signal V0, another terminal of the photodiode outputs the sensing signal Vout.

Figure 3A:
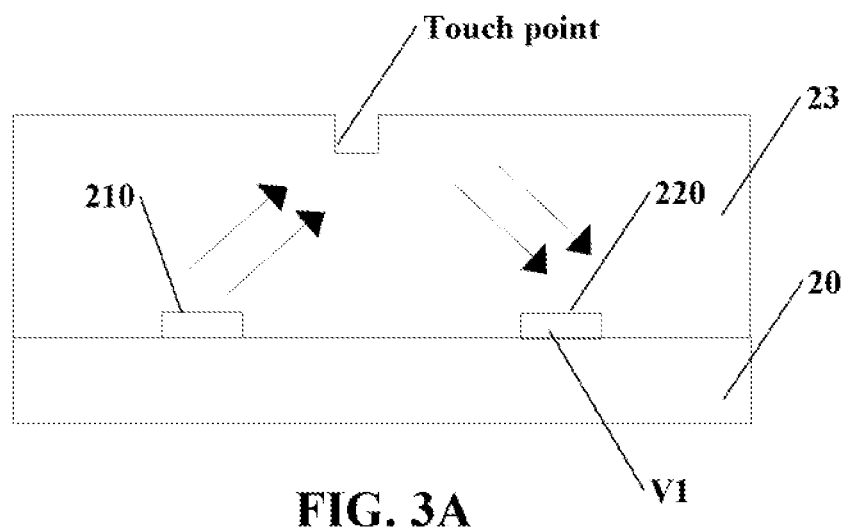
FIGS. 3A and 3B illustrate a process of detecting a touch in some embodiments according to the present disclosure.
Figure 3B:
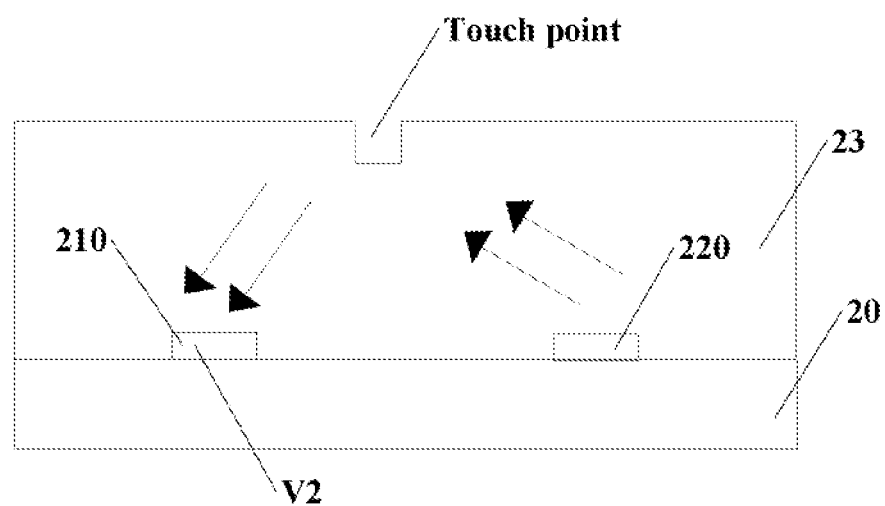

In some embodiments, each of the first component and the second component is a component that can be configured to emit light and can be alternatively configured to detect light. For example, in some embodiments, each of the first component and the second component is a photosensing light emitting diode, such as a photodiode. FIGS. 3A and 3B illustrate a process of detecting a touch in some embodiments according to the present disclosure. Referring to FIG. 3A and FIG. 3B, the first component is a first photodiode 210, and the second component is a second photodiode 220. Referring to FIG. 3A, the first photodiode 210 is configured to emit light and the second photodiode 220 is configured to detect light. At least a portion of light emitted from the first photodiode 210 and reflected by the surface of the elastic layer 23 is received by the second photodiode 220, the second photodiode 220 outputs a first voltage signal V1. The equivalent circuit for the first photodiode 210 is illustrated in FIG. 6, and the equivalent circuit for the second photodiode 220 is illustrated in FIG. 7.

When the first photodiode 210 is switched to be a light detecting component, and the second photodiode 220 is switched to be a light emitting component, the equivalent circuit for the first photodiode 210 is illustrated in FIG. 7, and the equivalent circuit for the second photodiode 220 is illustrated in FIG. 6. Referring to FIG. 3B, the second photodiode 220 is configured to emit light and the first photodiode 210 is configured to detect light. At least a portion of light emitted from the second photodiode 220 and reflected by the surface of the elastic layer 23 is received by the first photodiode 210, the first photodiode 210 outputs a second voltage signal V2.

In some embodiments, by comparing the intensity of the first voltage signal V1 and the intensity of the second voltage signal V2, the touch position (the position where the force is applied on the sensing apparatus) can be determined. By calibrating the sensing signals with a plurality of reference signals respectively corresponding to a plurality of reference pressures, the pressure applied to the sensing apparatus can be determined.

Figure 5:
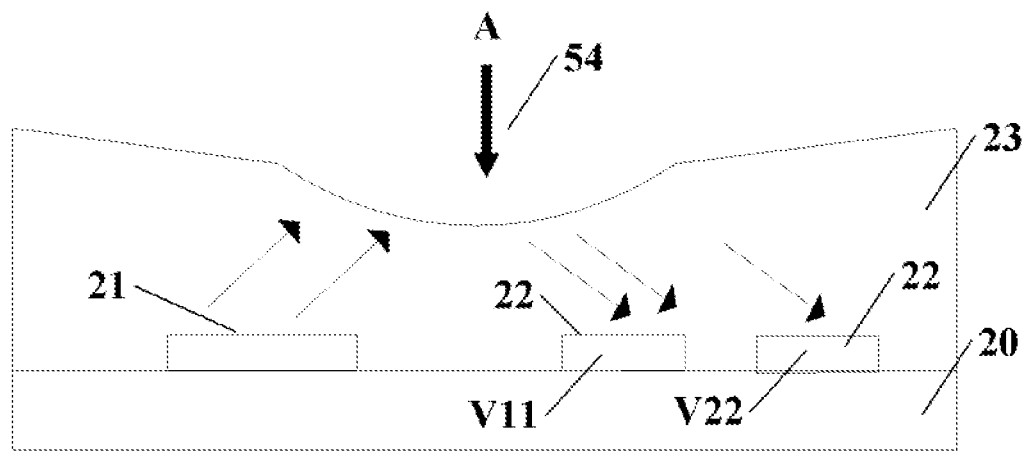
FIG. 5 is a diagram illustrating the structure of a sensing apparatus in some embodiments according to the present disclosure.

In some embodiments, a total number of components in a respective one of the plurality of sensing units configured to emit light is one and a total number of components in the respective one of the plurality of sensing units configured to detect light is two. FIG. 5 is a diagram illustrating the structure of a sensing apparatus in some embodiments according to the present disclosure. Referring to FIG. 5, a total number of the first component 21 in the respective one of the plurality of sensing units is one, and a total number of the second component 22 in the respective one of the plurality of sensing units is two. The first one of the second component 22 is configured to output a first sensing signal V11, and the second one of the second component 22 is configured to output a second sensing signal V22. Optionally, by comparing the intensity of the first voltage signal V11 and the intensity of the second voltage signal V22, the touch position (the position where the force is applied on the sensing apparatus) can be determined. By calibrating the sensing signals with a plurality of reference signals respectively corresponding to a plurality of reference pressures, the pressure applied to the sensing apparatus can be determined. By having two sensing signals output from the respective one of the plurality of sensing units, the sensing apparatus can not only detect Whether a force is applied, but also detect the touch position and a magnitude of the applied pressure.

Optionally, a total number of components in a respective one of the plurality of sensing units configured to emit light is one and a total number of components in the respective one of the plurality of sensing units configured to detect light is one.

Optionally, a total number of components in a respective one of the plurality of sensing units configured to emit light is two or more and a total number of components in the respective one of the plurality of sensing units configured to detect light is two or more. By having multiple light emitting components and multiple light detecting components in the respective one of the plurality of sensing units, the light detecting accuracy can be greatly enhanced. In example, a total number of components in the respective one of the plurality of sensing units configured to emit light is two and a total number of components in the respective one of the plurality of sensing units configured to detect light is also two. Each of the two light detecting components is configured to independently detect reflected light from two light emitting components, and each of the two light emitting components independently emits light, reflection of which on the surface of the elastic layer 23 is independently affected by the deformation of the elastic layer 23.

Referring to FIG. 8, a respective one of the plurality of sensing units includes multiple ones of light detecting components arranged in a form of an array. Optionally, the sensing apparatus having the array of light detecting components can be encapsulated in a way such that adjacent sensing units of the plurality of sensing units do not interfere with each other. Optionally, the elastic layer includes a plurality of elastic blocks respectively in the plurality of sensing units, and adjacent elastic blocks of the plurality of elastic blocks are spaced apart from each other. Optionally, the elastic layer is a continuous integral layer overlaying the plurality of sensing units altogether, the integral structure is then divided into the plurality of sensing units during an encapsulating process.

In some embodiments, the plurality of sensing units are connected together to form an integral array of circuits. Optionally, the plurality of sensing units are connected in parallel. Optionally, the plurality of sensing units are connected in series.

In some embodiments, the plurality of sensing units are not connected to each other, but independent units configured to independently detect deformation of the elastic layer at each local position, thereby independently detecting a touch.

In some embodiments, in the sensing apparatus having the plurality of sensing units, a touch position can be detected by detecting the sensing signal output from the respective one of the plurality of sensing units to determine which sensing unit(s) is applied with a force. Optionally, the magnitude of the pressure applied to the sensing apparatus can be detected by detecting a sum of the sensing signals from the plurality of sensing units, and comparing the sum of the sensing signals with a reference database.

In some embodiments, in the sensing apparatus having the plurality of sensing units, presence or absence of a touch, the touch position, and the magnitude of the pressure applied, can be determined based on the sensing signal output from the respective one of the plurality of sensing units individually. A high-resolution touch detection can be achieved, particularly suitable for applications in medical devices and biotechnology applications. In one example, the sensing apparatus according to the present disclosure can be used in combination with a nano-probe to search and track the movement of the nano-probe.

As shown in FIG. 8, the plurality of sensing unit SU may be arranged in various appropriate forms of arrays, such as a rectangular array (8-1), a rhombohedral array (8-2), and a hexagonal array (8-3). By having a high-density and high-resolution array arrangement, a relatively high resolution can be achieved, e.g., higher than 1 mm resolution.

Figure 9:
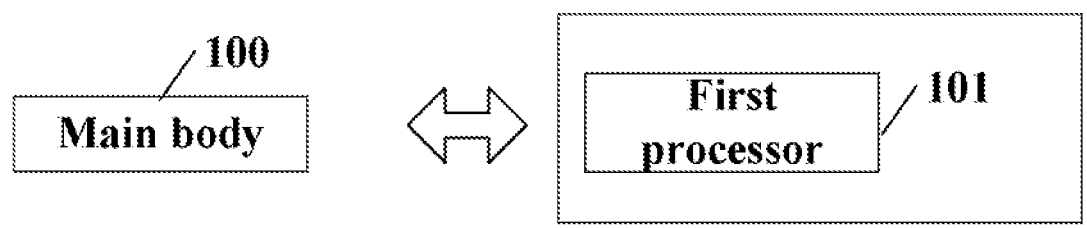
FIG. 9 is a diagram illustrating the structure of a sensing apparatus in some embodiments according to the present disclosure.

In some embodiments, the sensing apparatus further includes a sensing circuit configured to receive the sensing signal from the second component of a respective one of the plurality of sensing units, and determine the degree of the deformation of the elastic layer at each local position based on the sensing signal from the second component of the respective one of the plurality of sensing units. FIG. 9 is a diagram illustrating the structure of a sensing apparatus in some embodiments according to the present disclosure. Referring to FIG. 9, the sensing apparatus includes a main body 100 and a first processor 101 coupled to the main body 100. The main body 100 may include the base substrate, the elastic layer, and the plurality of sensing units as described above. In some embodiments, the first processor 101 is configured to receive the sensing signal from the second component of the respective one of the plurality of sensing units, and determine the degree of the deformation of the elastic layer at each local position based on the sensing signal from the second component of the respective one of the plurality of sensing units.

FIG. 10 is a diagram illustrating the structure of a sensing apparatus in some embodiments according to the present disclosure. Referring to FIG. 10, the sensing apparatus in some embodiments includes a memory 111 configured to store a plurality of reference sensing signals corresponding to different degrees of deformation, and a second processor 112 configured to receive the sensing signal from the second component of the respective one of the plurality of sensing units, compare the sensing signal from the second component of the respective one of the plurality of sensing units with the plurality of reference sensing signals, and determine the degree of the deformation of the elastic layer at each local position based on comparison between the sensing signal from the second component of the respective one of the plurality of sensing units and the plurality of reference sensing signals.

Each of the first processor 101, the memory 111, and the second processor 112, can be disposed in the sensing apparatus. Alternatively, each of the first processor 101, the memory 111, and the second processor 112, can be disposed remotely, e.g., in cloud or a remote server. In one example, the first processor 101, the memory 111, and the second processor 112 are disposed in a server, which is wirelessly connected to the main body 110. The server optionally further includes a wireless communication unit configured to receive and transmit data between the main body and the server. Optionally, the server further includes a deep learning training unit to enhance the efficiency and accuracy of pressure detection. Optionally, the first processor 101 and the second processor 112 are a same processor.

In some embodiments, the base substrate and the elastic layer of the sensing apparatus are made of flexible materials, with the light emitting components and light detecting components embedded therein. The resulting structure forms an integral artificial tactile sensing apparatus, having excellent adhering ability, particularly suitable for making artificial skins attached to the human skin or attached to prosthetic limb, simulating prosthetic touch.

In another aspect, the present disclosure provides a method of fabricating a sensing apparatus. FIG. 11 is a flow chart illustrating a method of fabricating a sensing apparatus in some embodiments according to the present disclosure. Referring to FIG. 11, the method in some embodiments includes forming a plurality of sensing units on a base substrate, a respective one of the plurality of sensing units formed to include a first component configured to emit light and a second component configured to detect light; and forming an elastic layer on a side of the plurality of sensing units distal to the base substrate and configured to undergo a deformation upon a touch, at least a portion of light emitted from the first component being reflected by a surface of the elastic layer, the second component being formed to detect light reflected by the surface of the elastic layer and output a sensing signal, an intensity of which being correlated to a degree of the deformation of the elastic layer at a local position. Optionally, the first component is formed as a point light source. Optionally, the first component is formed to emit substantially collimated light.

In some embodiments, the method further includes forming a processor configured to receive the sensing signal from the second component of a respective one of the plurality of sensing units, and determine the degree of the deformation of the elastic layer at each local position based on the sensing signal front the second component of the respective one of the plurality of sensing units. FIG. 12 is a flow chart illustrating a method of fabricating a sensing apparatus in some embodiments according to the present disclosure. Referring to FIG. 12, the method in some embodiments further includes forming a memory configured to store a plurality of reference sensing signals corresponding to different degrees of deformation; and forming a second processor configured to receive the sensing signal from the second component of the respective one of the plurality of sensing units, compare the sensing signal from the second component of the respective one of the plurality of sensing units with the plurality of reference sensing signals, and determine the degree of the deformation of the elastic layer at each local position based on comparison between the sensing signal from the second component of the respective one of the plurality of sensing units and the plurality of reference sensing signals.

In another aspect, the present disclosure further provides a method of detecting a touch. In some embodiments, the method includes emitting light from a first component of a respective one of a plurality of sensing units, reflecting at least a portion of light emitted from the first component by a surface of an elastic layer; detecting light reflected by the surface of the elastic layer by a second component of the respective one of the plurality of sensing units; and outputting a first sensing signal from the second component of the respective one of the plurality of sensing units; wherein an intensity of the first sensing signal is correlated to a degree of the deformation of the elastic layer at a local position.

FIG. 13 is a flow chart illustrating a method of detecting a touch in some embodiments according to the present disclosure. Referring to FIG. 13, the method in some embodiments includes outputting a first sensing signal from the second component of a respective one of the plurality of sensing units upon receiving light reflected by a surface of the elastic layer by the second component; and determining a degree of the deformation of the elastic layer at each local position based on the sensing signal from the second component.

In some embodiments, the intensity of the sensing signal output from the second component can be described or expressed using a detectable value or a value that directly reflecting the intensity of light received by the second component. Further, the value describing the intensity of light received by the second component reflects the degree of the deformation of the elastic layer at the local position. In one example, the value is zero, which denotes that the second component does not receive any detectable light from the first component. Based on the magnitude of the sensing signal, a processor determines the intensity of light received by the second component, and in turn determines whether a force is applied to the elastic layer at the local position, and if so, the position and magnitude of the force being applied.

FIG. 14 is a flow chart illustrating a method of detecting a touch in some embodiments according to the present disclosure. Referring to FIG. 14, the method in some embodiments includes outputting a first sensing signal from the second component of a respective one of the plurality of sensing units upon receiving light reflected by a surface of the elastic layer by the second component; based on a plurality of reference sensing signals corresponding to different degrees of deformation stored in a memory, comparing the sensing signal from the second component of the respective one of the plurality of sensing units with the plurality of reference sensing signals; and determining the degree of the deformation of the elastic layer at each local position based on comparison between the sensing signal from the second component of the respective one of the plurality of sensing units and the plurality of reference sensing signals. The present method provides a high-resolution touch detection, particularly suitable for applications in medical devices and biotechnology applications.

Figure 16:
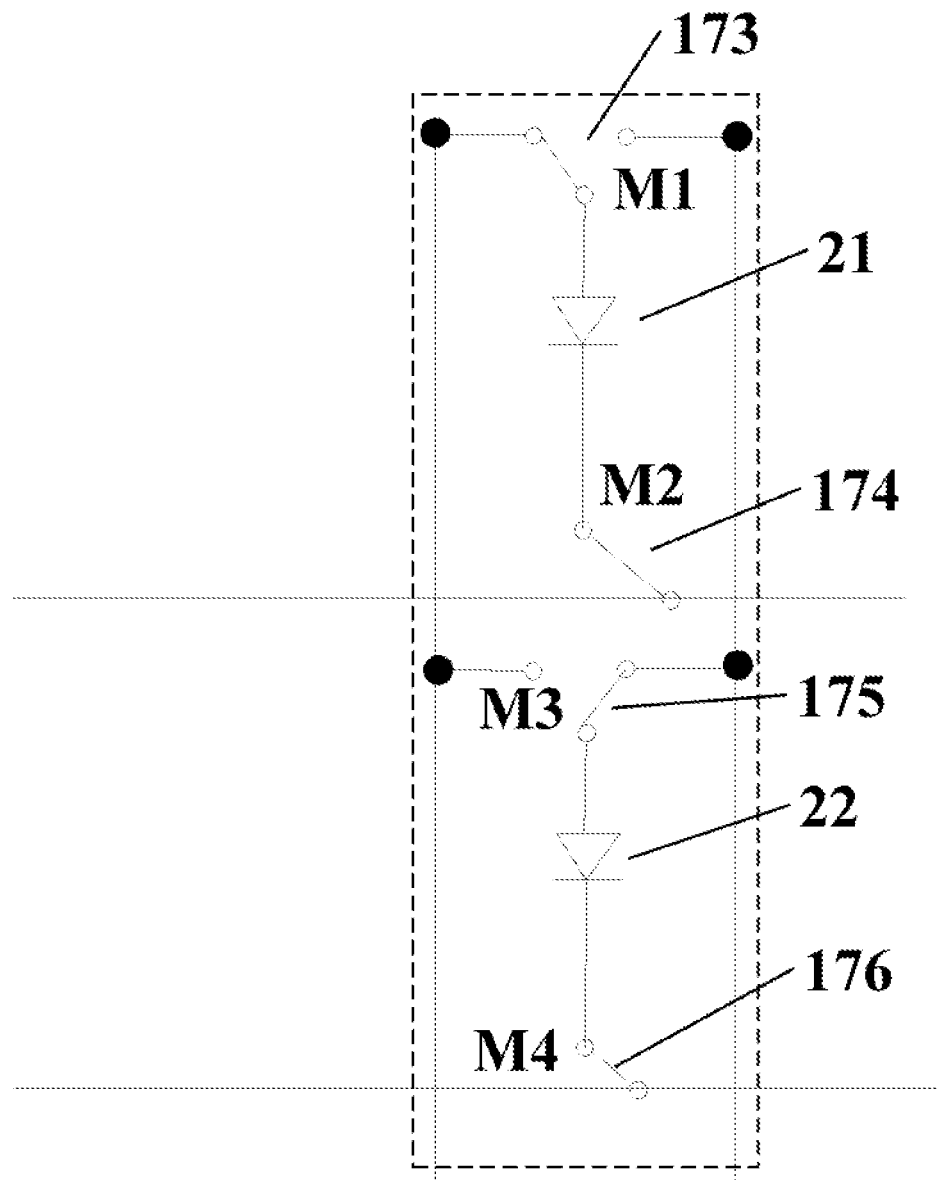
FIG. 16 is a circuit diagram of a sensing circuit in some embodiments according to the present disclosure.

In some embodiments, the sensing apparatus includes a sensing circuit. FIG. 15 is a circuit diagram of a sensing circuit in some embodiments according to the present disclosure, FIG. 16 is a circuit diagram of a sensing circuit in some embodiments according to the present disclosure. FIG. 16 shows the structure of a sensing unit SU in FIG. 15. Referring to FIG. 15 and FIG. 16, the sensing circuit in some embodiments includes an input voltage signal line a first output voltage signal line Vout1; a reference voltage signal line V0; and a ground voltage signal line 0V. The sensing circuit further includes a plurality of sensing units SU. A respective one of the plurality of sensing units SU includes a first component 21 and a second component 22. Further, the sensing circuit in some embodiments further includes a first selector switch 173 configured to selectively couple a first terminal of the first component 21 to one of the input voltage signal line Vin or the first output voltage signal line Vout1; a second selector switch 174 configured to selectively couple a second terminal of the first component 21 to one of the reference voltage signal line V0 or the ground voltage signal line 0V; a third selector switch 175 configured to selectively couple a first terminal of the second component 22 to one of the input voltage signal line Vin or the first output voltage signal line Vout1; and a fourth selector switch 176 configured to selectively couple a second terminal of the second component 22 to one of the reference voltage signal line V0 or the ground voltage signal line 0V.

In some embodiments, the first component 21 is configured to emit light when a voltage level at the first terminal of the first component 21 is higher than a voltage level at the second terminal of the first component 21 to generate a current flowing from the first terminal of the first component 21 to the second terminal of the first component 21; and the second component 22 is configured to detect light when a voltage level at the second terminal of the second component 22 is higher than a voltage level at the first terminal of the second component 22 to generate a photocurrent flowing from the second terminal of the second component 22 to the first terminal of the second component 22.

Optionally, each of the first selector switch 173, the second selector switch 174, the third selector switch 175, and the fourth selector switch 176 is a double-pole switch.

Optionally, each of the first selector switch 173 and the third selector switch 175 is a double-pole switch, and each of the second selector switch 174 and the fourth selector switch 176 is a single-pole switch. Optionally, the single-pole switch (e.g., the second selector switch 174 and the fourth selector switch 176) selectively controls a connection with the reference voltage signal line V0 or the ground voltage signal line 0V.

Optionally, the selector switch includes a triode. Optionally, the selector switch includes a NMOS transistor. Optionally, the selector switch includes a PMOS transistor.

In some embodiments, the method includes, under a plurality of control signals (e.g., control signals M1 to M4 as shown in FIG. 16) sequentially selectively coupling terminals of the first components 21 and the second components 22 of the plurality of sensing units SU respectively to various signal lines at a given time interval. For example, under the control signal M1, the first selector switches 173 in the plurality of sensing units SU are configured to sequentially selectively coupling first terminals of first components 21 of the plurality of sensing units SU to an input voltage signal line Vin at a given time interval. Under the control signal M2, the second selector switches 174 in the plurality of sensing units SU are configured to sequentially selectively coupling second terminals of first components 21 of the plurality of sensing units SU to a ground voltage signal line 0V at a given time interval. Under the control signal M3, the third selector switches 175 in the plurality of sensing units SU are configured to sequentially selectively coupling first terminals of second components 22 of the plurality of sensing units SU to a first output voltage signal line Vout1 at a given time interval. Under the control signal M4, the fourth selector switches 176 in the plurality of sensing units SU are configured to sequentially selectively coupling second terminals of second components 22 of the plurality of sensing units SU to a reference voltage signal line V0 at a given time interval. The voltage level at the first terminal of the first component 21 is an input voltage level v1, and the voltage level at the second terminal of the first component 21 is zero, and the first component 21 is forwardly conducted, and emits light. The voltage level at the first terminal of the second component 22 is a voltage level v2, and the voltage level at the second terminal of the second component 22 is a reference voltage level v0. When the second component 22 detects a photon, a reverse photocurrent is generated due to the photovoltaic effect. Accordingly, the sensing circuit detects a first output voltage having a voltage level of v3. Optionally, the sensing circuit further includes an amplifier downstream of the first output voltage signal line Vout1 to increase detection accuracy. When the elastic layer is subject to a force, the elastic layer undergoes a deformation, resulting in a change in the intensity of light received by the second component 22. The voltage level of the first output voltage changes to a voltage level of v4. By comparing the voltage level v4 with the voltage level v3, it can be determined that at least one of the plurality of sensing units SU is subject to the force.

Figure 17:
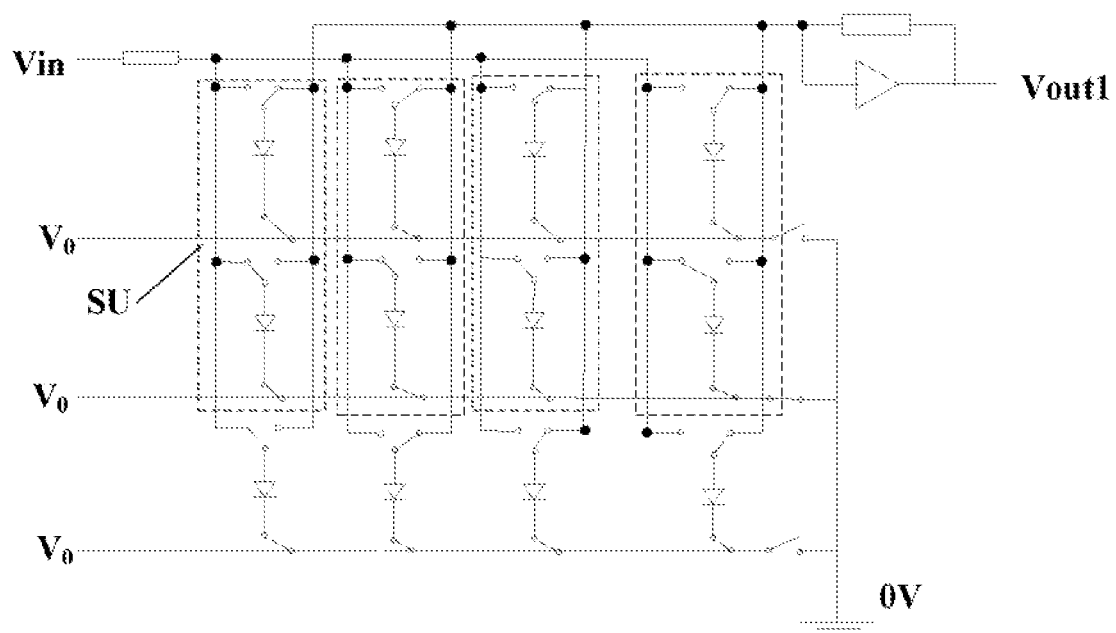
FIG. 17 is a circuit diagram of a sensing circuit in some embodiments according to the present disclosure.
Figure 18:
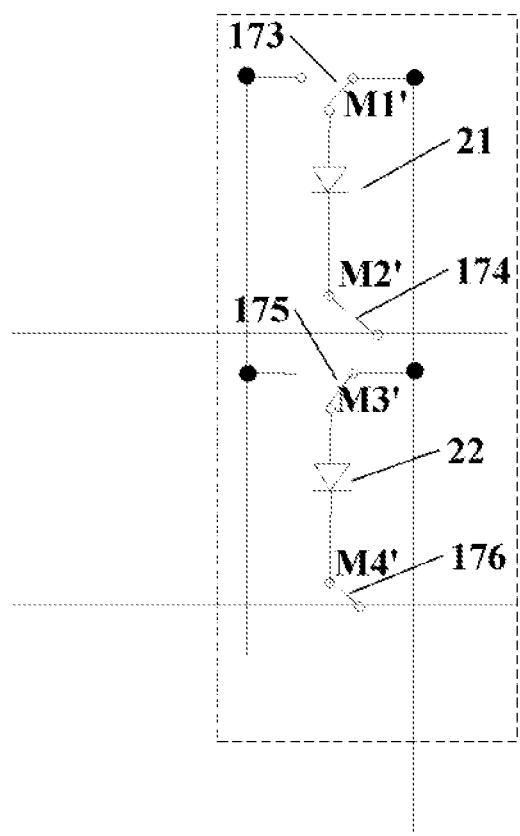
FIG. 18 is a circuit diagram of a sensing circuit in some embodiments according to the present disclosure.

In some embodiments, the first component 21 is configured to detect light when a voltage level at the second terminal of the first component 21 is higher than a voltage level at the first terminal of the first component 21 to generate a photocurrent flowing from the second terminal of the first component 21 to the first terminal of the first component 21; and the second component 22 is configured to emit light when a voltage level at the first terminal of the second component 22 is higher than a voltage level at the second terminal of the second component 22 to generate a current flowing from the first terminal of the second component 22 to the second terminal of the second component 22. FIG. 17 is a circuit diagram of a sensing circuit in some embodiments according to the present disclosure. FIG. 18 is a circuit diagram of a sensing circuit in some embodiments according to the present disclosure. FIG. 18 shows the structure of a sensing unit SU in FIG. 17. Referring to FIG. 17 and FIG. 18, each of the first selector switch 173, the second selector switch 174, the third selector switch 175, and the forth selector switch 176 is a double-pole switch.

Accordingly, in some embodiments, the method further includes emitting light from the second component 22 of a respective one of a plurality of sensing units SU; reflecting at least a portion of light emitted from the second component 22 by the surface of the elastic layer; detecting light reflected by the surface of the elastic layer by the first component 21 of the respective one of the plurality of sensing units SU; and outputting a second sensing signal from the first component 21 of the respective one of the plurality of sensing units SU. Optionally, the intensity of the second sensing signal is correlated to a degree of the deformation of the elastic layer at a local position.

In some embodiments, the method includes, under a plurality of control signals (e.g., control signals M1' to M4' as shown in FIG. 18), sequentially selectively coupling terminals of the first components 21 and the second components 22 of the plurality of sensing units SU respectively to various signal lines at a given time interval. For example, under the control signal M1', the first selector switches 173 in the plurality of sensing units SU are configured to sequentially selectively coupling first terminals of first components 21 of the plurality of sensing units SU to a first output voltage signal line Vout1 at a given time interval. Under the control signal M2', the second selector switches 174 in the plurality of sensing units SU are configured to sequentially selectively coupling second terminals of first components 21 of the plurality of sensing units SU to a reference voltage signal line V0 at a given time interval. Under the control signal M3', the third selector switches 175 in the plurality of sensing units SU are configured to sequentially selectively coupling first terminals of second components 22 of the plurality of sensing units SU to an input voltage signal line Vin at a given time interval. Under the control signal M4', the fourth selector switches 176 in the plurality of sensing units SU are configured to sequentially selectively coupling second terminals of second components 22 of the plurality of sensing units SU to a ground voltage signal line 0V at a given time interval. The voltage level at the first terminal of the second component 22 is an input voltage level v1, and the voltage level at the second terminal of the second component 22 is zero, and the second component 22 is forwardly conducted, and emits light. The voltage level at the first terminal of the first component 21 is a voltage level v2, and the voltage level at the second terminal of the first component 21 is a reference voltage level v0. When the first component 21 detects a photon, a reverse photocurrent is generated due to the photovoltaic effect. Accordingly, the sensing circuit detects a first output voltage having a voltage level of v3. When the elastic layer is subject to a force, the elastic layer undergoes a deformation, resulting in a change in the intensity of light received by the first component 21. The voltage level of the first output voltage changes to a voltage level of v4. By comparing the voltage level v4 with the voltage level v3, it can be determined that at least one of the plurality of sensing units SU is subject to the force.

In some embodiments, the sensing apparatus is operated in a time-division driving mode including a first mode and a second mode. In the first mode (e.g., during a first time period T1), the sensing apparatus is under the control of control signals M1 to M4. In the second mode (e.g., during a second time period T2), the sensing apparatus is under the control of control signals M1' to M4'. Specifically, in the first mode, the control signal M1 controls the first selector switches 173 to sequentially selectively coupling first terminals of first components 21 to an input voltage signal line Vin at a given time interval, the control signal M2 controls the second selector switches 174 to sequentially selectively coupling second terminals of first components 21 to a ground voltage signal line 0V at a given time interval, the control signal M3 controls the third selector switches 175 to sequentially selectively coupling first terminals of second components 22 to a first output voltage signal line Vout1 at a given time interval, the control signal M4 controls the fourth selector switches 176 to sequentially selectively coupling second terminals of second components 22 to a reference voltage signal line V0 at a given time interval. Specifically, in the second mode, the control signal M1' controls the first selector switches 173 to sequentially selectively coupling first terminals of first components 21 to a first output voltage signal line Vout1 at a given time interval, the control signal M2' controls the second selector switches 174 to sequentially selectively coupling second terminals of first components 21 to a reference voltage signal line V0 at a given time interval, the control signal M3' controls the third selector switches 175 to sequentially selectively coupling first terminals of second components 22 to an input voltage signal line Vin at a given time interval, the control signal M4' controls the fourth selector switches 176 to sequentially selectively coupling second terminals of second components 22 to a ground voltage signal line 0V at a given time interval. By detecting a first output voltage Vt1 in the first mode (during the first time period t1) and a second output voltage Vt2 in the second mode (during, the second time period t2), the touch position and touch pressure can be determined.

Optionally, each of the first selector switch 173, the second selector switch 174, the third selector switch 175, and the fourth selector switch 176 is a double-pole switch.

Optionally, each of the first selector switch 173 and the third selector switch 175 is a double-pole switch, and each of the second selector switch 174 and the fourth selector switch 176 is a single-pole switch. Optionally, the single-pole switch (e.g., the second selector switch 174 and the fourth selector switch 176) selectively controls a connection with the reference voltage signal line V0 or the ground voltage signal line 0V.

Figure 19:
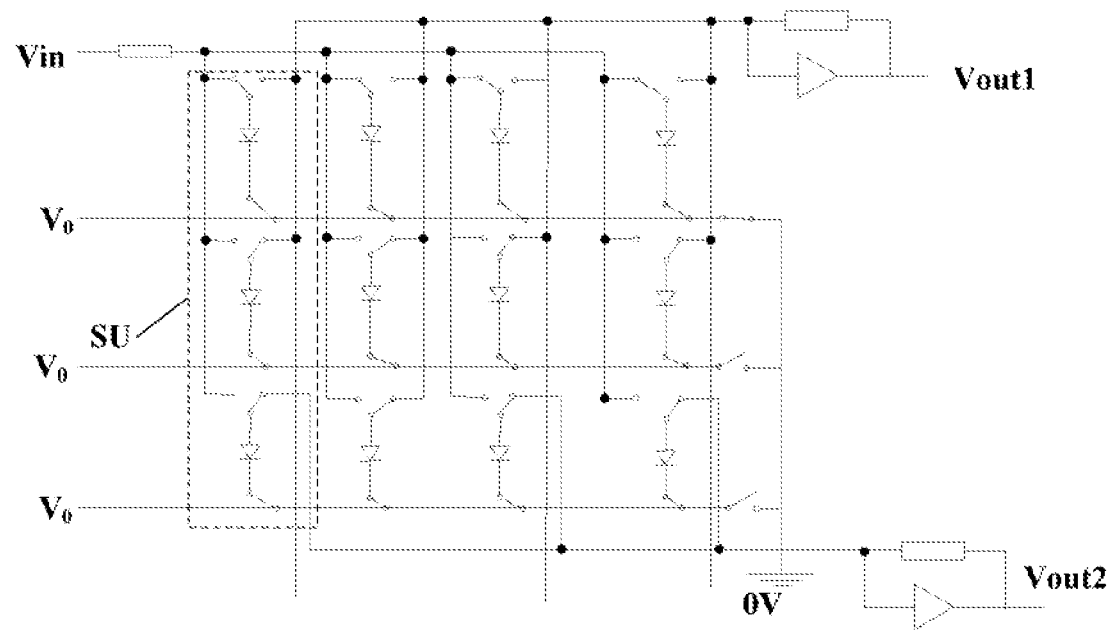
FIG. 19 is a circuit diagram of a sensing circuit in some embodiments according to the present disclosure.
Figure 20:
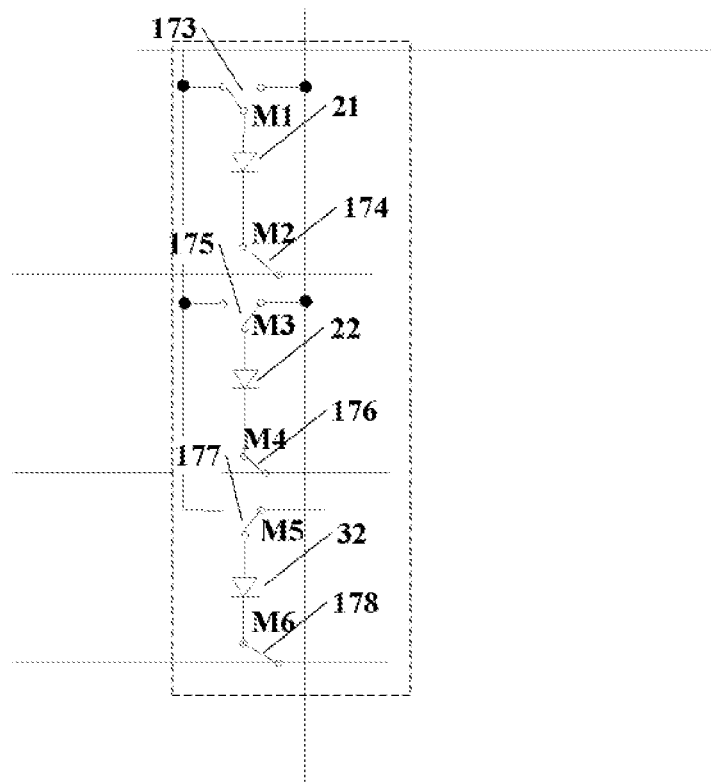
FIG. 20 is a circuit diagram of a sensing circuit in some embodiments according to the present disclosure.

In some embodiments, a respective one of the plurality of sensing units SU further includes a third component. FIG. 19 is a circuit diagram of a sensing circuit in some embodiments according to the present disclosure. FIG. 20 is a circuit diagram of a sensing circuit in some embodiments according to the present disclosure. Referring to FIG. 19 and FIG. 20, the sensing apparatus in some embodiments further comprises a second output voltage signal line Vout2, and the respective one of the plurality of sensing units SU further includes a third component 32. Optionally, the sensing circuit further includes a fifth selector switch 177 configured to selectively couple a first terminal of the third component 32 to one of the input voltage signal line or the second output voltage signal line Vout2; and a sixth selector switch 178 configured to selectively couple a second terminal of the third component 32 to one of the reference voltage signal line V0 or the ground voltage signal line 0V. Optionally, the third component 32 is configured to detect light when a voltage level at the second terminal of the third component 32 is higher than a voltage level at the first terminal of the third component 32 to generate a photocurrent flowing from the second terminal of the third component 32 to the first terminal of the third component 32.

Accordingly, the method in some embodiments includes emitting light from a first component of a respective one of a plurality of sensing units SU; reflecting at least a portion of light emitted from the first component 21 by a surface of an elastic layer; detecting light reflected by the surface of the elastic layer by a second component 22 of the respective one of the plurality of sensing units; outputting a first sensing signal from the second component 22 of the respective one of the plurality of sensing units; further detecting light reflected by the surface of the elastic layer by a third component 32 of the respective one of the plurality of sensing units SU, and outputting a third sensing signal from the third component 32 of the respective one of the plurality of sensing units. An intensity of the first sensing signal and an intensity of the third sensing signal are independently correlated to a degree of the deformation of the elastic layer at a local position. Optionally, by comparing the first sensing signal and the third sensing signal, a touch position and touch pressure can be determined more accurately. Optionally, the first sensing signal and the third sensing signal are compared with a plurality of reference signals corresponding to a plurality of touch positions, a touch position and touch pressure can be determined more accurately.

In some embodiments, the method further includes, under a plurality of control signals (e.g., control signals M1 to M6 as shown in FIG. 20), sequentially selectively coupling terminals of the first components 21, the second components 22, and the third component 32 of the plurality of sensing units SU respectively to various signal lines at a given time interval. For example, under the control signal M1, the first selector switches 173 in the plurality of sensing units SU are configured to sequentially selectively coupling first terminals of first components 21 of the plurality of sensing units SU to an input voltage signal line Vin at a given time interval. Under the control signal M2, the second selector switches 174 in the plurality of sensing units SU are configured to sequentially selectively coupling second terminals of first components 21 of the plurality of sensing units SU to a ground voltage signal line 0V at a given time interval. Under the control signal M3, the third selector switches 175 in the plurality of sensing units SU are configured to sequentially selectively coupling first terminals of second components 22 of the plurality of sensing units SU to a first output voltage signal line Vout1 at a given time interval. Under the control signal M4, the fourth selector switches 176 in the plurality of sensing units SU are configured to sequentially selectively coupling second terminals of second components 22 of the plurality of sensing units SU to a reference voltage signal line V0 at a given time interval. Under the control signal M5, the fifth selector switch 177 in the plurality of sensing units SU are configured to sequentially selectively coupling first terminals of third components 32 of the plurality of sensing units SU to a second output voltage signal line Vout2 at a given time interval. Under the control signal M6, the sixth selector switch 178 in the plurality of sensing units SU are configured to sequentially selectively coupling second terminals of third components 32 of the plurality of sensing units SU to the reference voltage signal line V0 at a given time interval. A first output voltage from the first output voltage signal line Vout1 and a second output voltage from the second output voltage signal line Vout2 can be detected to determine a touch position and a touch pressure.

Optionally, each of the first selector switch 173, the second selector switch 174, the third selector switch 175, the fourth selector switch 176, the fifth selector switch 177, and the sixth selector switch 178 is a double-pole switch.

Optionally, each of the first selector switch 173, the third selector switch 175, and the fifth selector switch 177 is a double-pole switch, and each of the second selector switch 174, the fourth selector switch 176, and the sixth selector switch 178 is a single-pole switch. Optionally, the single-pole switch (e.g., the second selector switch 174, the fourth selector switch 176, and the sixth selector switch 178)

selectively controls a connection with the reference voltage signal line V0 or the ground voltage signal line 0V.

FIG. 21 is a flow chart illustrating a method of detecting a touch in some embodiments according to the present disclosure. Referring to FIG. 21, the method in some embodiments includes sequentially inputting a first control signal to first selector switches at a given time interval, sequentially inputting a second control signal to second selector switches at a given time interval, sequentially inputting a third control signal to third selector switches at a given time interval, sequentially inputting a fourth control signal to fourth selector switches at a given time interval; detecting in real time a first output voltage from the first output voltage signal line using a voltage detector when the first control signal and the second control signal are inputted; and counting a time duration during which the first output voltage undergoes a change exceeding a threshold value. Optionally, the method further includes one or a combination of the following steps: (1) comparing the time duration with time points at which the plurality of sensing units respectively receiving the first control signal to determine a sensing unit subject to touch, and (2) comparing a change in a voltage level of the first output voltage during the time duration with a plurality of reference voltage levels to determine a touch pressure.

In one example, and referring to FIG. 15 and FIG. 16, during a first time period T1, the control signal M1 controls the first selector switches 173 to sequentially selectively coupling first terminals of first components 21 to an input voltage signal line Vin at a given time interval, the control signal M2 controls the second selector switches 174 to sequentially selectively coupling second terminals of first components 21 to a ground voltage signal line 0V at a given time interval, the control signal M3 controls the third selector switches 175 to sequentially selectively coupling first terminals of second components 22 to a first output voltage signal line Vout1 at a given time interval, and the control signal M4 controls the fourth selector switches 176 to sequentially selectively coupling second terminals of second components 22 to a reference voltage signal line V0 at a given time interval. The first component 21 is a light emitting component, and the second component 22 is a light detecting component. In one example, the first component 21 is a light emitting diode and the second component 22 is a photodiode. In another example, the first component 21 is a photodiode and the second component 22 is also a photodiode. The photodiode is capable of generating a reverse photocurrent due to the photovoltaic effect when exposed to light, thereby outputting a first output voltage signal.

By comparing the time duration with time points at which the plurality of sensing units respectively receiving the first control signal, a position of a sensing unit subject to touch can be determined. Because a respective one of the plurality of sensing units receives the first control signal at different time points in a given order, the comparison can effectively reveal the exact sensing unit that is subject to touch.

By comparing a change in a voltage level of the first output voltage during the time duration with a plurality of reference voltage levels, a touch pressure can be determined. The plurality of reference voltage levels can be stored in a memory. Alternatively, a correlation function can be stored in a memory for determining the touch pressure. Optionally, the plurality of reference voltage levels or the correlation function can be stored in cloud or a remote server. Optionally, the plurality of reference voltage levels or the correlation function can be optimized based on a deep learning training unit.

In some embodiments, to further enhance the detection accuracy, each of the first component and the second component can switch between being a light emitting component and a light detecting component. Optionally, each of the first component and the second component is a photodiode that can be configured to be a light emitting component or configured to be a light detecting component. FIG. 22 is a flow chart illustrating a method of detecting a touch in some embodiments according to the present disclosure. Referring to FIG. 22, the method includes operating the touch detection in a time-division driving mode including a first mode and a second mode. In the first mode, the method includes sequentially inputting a first control signal to first selector switches at a given time interval, sequentially inputting a second control signal to second selector switches at a given time interval, sequentially inputting a third control signal to third selector switches at a given time interval, sequentially inputting a fourth control signal to fourth selector switches at a given time interval; and detecting in real time a first output voltage from the first output voltage signal line using a voltage detector when the first control signal, the second control signal, the third control signal, and the fourth control signal are inputted. In the second mode, the method includes in a second mode, sequentially inputting a fifth control signal to first selector switches at a given time interval, sequentially inputting a sixth control signal to second selector switches at a given time interval, sequentially inputting a seventh control signal to third selector switches at a given time interval, sequentially inputting an eighth control signal to fourth selector switches at a given time interval; and detecting in real time a second output voltage from the first output voltage signal line using the voltage detector when the fifth control signal, the sixth control signal, the seventh control signal, and the eighth control signal are inputted. The method further includes counting a time duration during which the first output voltage and the second output voltage respectively undergo a change exceeding a threshold value; and one or a combination of the following: (1) comparing the time duration with time points at which the plurality of sensing units respectively receiving control signals to determine a sensing unit subject to touch; and (2) comparing changes in voltage levels of the first output voltage and the second output voltage during the time duration with a plurality of first reference voltage levels and a plurality of second reference voltage levels respectively to determine a touch pressure.

Referring to FIG. 15 and FIG. 16, in the first mode (e.g., during a first time period T1), the control signal M1 controls the first selector switches 173 to sequentially selectively coupling first terminals of first components 21 to an input voltage signal line Vin at a given time interval, the control signal M2 controls the second selector switches 174 to sequentially selectively coupling second terminals of first components 21 to a ground voltage signal line 0V at a given time interval, the control signal M3 controls the third selector switches 175 to sequentially selectively coupling first terminals of second components 22 to a first output voltage signal line Vout1 at a given time interval, the control signal M4 controls the fourth selector switches 176 to sequentially selectively coupling second terminals of second components 22 to a reference voltage signal line V0 at a given time interval. Referring to FIG. 17 and FIG. 18, in the second mode (e.g., during a second time period T2), the control signal M1' controls the first selector switches 173 to sequentially selectively coupling first terminals of first components 21 to a first output voltage signal line Vout1 at a given time interval, the control signal M2' controls the second selector switches 174 to sequentially selectively coupling second terminals of first components 21 to a reference voltage signal line V0 at a given time interval, the control signal M3' controls the third selector switches 175 to sequentially selectively coupling first terminals of second components 22 to an input voltage signal line Vin at a given time interval, the control signal M4' controls the fourth selector switches 176 to sequentially selectively coupling second terminals of second components 22 to a ground voltage signal line 0V at a given time interval. By detecting a first output voltage Vt1 in the first mode (during the first time period t1) and a second output voltage Vt2 in the second mode (during the second time period t2), the touch position and touch pressure can be determined.

By comparing the time duration with time points at which the plurality of sensing units respectively receiving the control signals (e.g., the first control signal in the first mode or the fifth control signal in the second mode), a position of a sensing unit subject to touch can be determined. Because a respective one of the plurality of sensing units receives the first control signal or the fifth control signal at different time points in a given order, the comparison can effectively reveal the exact sensing unit that is subject to touch.

By comparing changes in voltage levels of the first output voltage and the second output voltage during the time duration with a plurality of first reference voltage levels and a plurality of second reference voltage levels respectively, a touch pressure can be determined with an enhanced accuracy. The plurality of reference voltage levels can be stored in a memory. Alternatively, a correlation function can be stored in a memory for determining the touch pressure. Optionally, the plurality of reference voltage levels or the correlation function can be stored in cloud or a remote server. Optionally, the plurality of reference voltage levels or the correlation function can be optimized based on a deep learning training unit.

In some embodiments, and referring to FIG. 19 and FIG. 20, the sensing apparatus in some embodiments further includes a second output voltage signal line Vout2, and the respective one of the plurality of sensing units SU further includes a third component 32. Optionally, the sensing circuit further includes a fifth selector switch 177 configured to selectively couple a first terminal of the third component 32 to one of the input voltage signal line or the second output voltage signal line Vout2; and a sixth selector switch 178 configured to selectively couple a second terminal of the third component 32 to one of the reference voltage signal line V0 or the ground voltage signal line 0V. Optionally, the third component 32 is configured to detect light when a voltage level at the second terminal of the third component 32 is higher than a voltage level at the first terminal of the third component 32 to generate a photocurrent flowing from the second terminal of the third component 32 to the first terminal of the third component 32.

Figure 23:
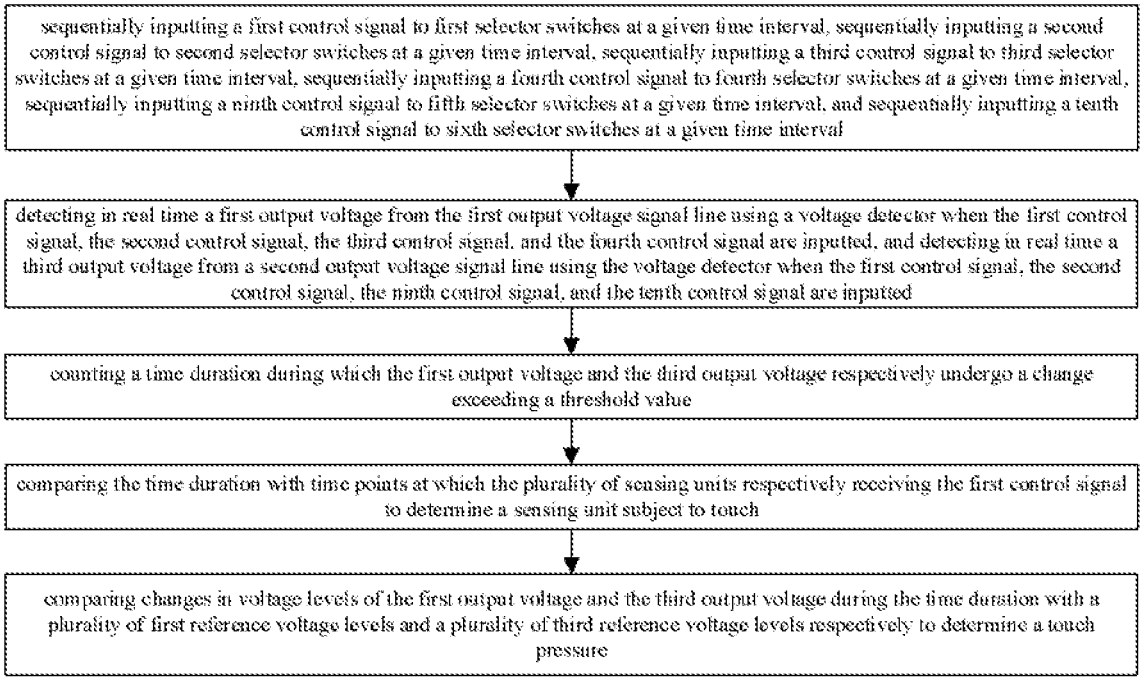
FIG. 23 is a flow chart illustrating a method of detecting a touch in some embodiments according to the present disclosure.

FIG. 23 is a flow chart illustrating a method of detecting a touch in some embodiments according to the present disclosure. Referring to FIG. 23, the method in some embodiment includes sequentially inputting a first control signal to first selector switches at a given time interval, sequentially inputting a second control signal to second selector switches at a given time interval, sequentially inputting a third control signal to third selector switches at a given time interval, sequentially inputting a fourth control signal to fourth selector switches at a given time interval, sequentially inputting a ninth control signal to fifth selector switches at a given time interval, and sequentially inputting a tenth control signal to sixth selector switches at a given time interval; detecting in real time a first output voltage from the first output voltage signal line using a voltage detector when the first control signal, the second control signal, the third control signal, and the fourth control signal are inputted, and detecting in real time a third output voltage from a second output voltage signal line using the voltage detector when the first control signal, the second control signal, the ninth control signal, and the tenth control signal are inputted; counting a time duration during which the first output voltage and the third output voltage respectively undergo a change exceeding a threshold value. Optionally, the method includes one or a combination of the following: (1) comparing the time duration with time points at which the plurality of sensing units respectively receiving the first control signal to determine a sensing unit subject to touch; and (2) comparing changes in voltage levels of the first output voltage and the third output voltage during the time duration with a plurality of first reference voltage levels and a plurality of third reference voltage levels respectively to determine a touch pressure In one example, and referring to FIG. 15 and FIG. 16, during a first time period T1, the control signal M1 controls the first selector switches 173 to sequentially selectively coupling first terminals of first components 21 to an input voltage signal line Vin at a given time interval; the control signal M2 controls the second selector switches 174 to sequentially selectively coupling second terminals of first components 21 to a ground voltage signal line 0V at a given time interval; the control signal M3 controls the third selector switches 175 to sequentially selectively coupling first terminals of second components 22 to a first output voltage signal line Vout1 at a given time interval; the control signal M4 controls the fourth selector switches 176 to sequentially selectively coupling second terminals of second components 22 to a reference voltage signal line V0 at a given time interval; the control signal M5 controls the fifth selector switch 177 to sequentially selectively coupling first terminals of third components 32 to a second output voltage signal line Vout2 at a given time interval; and the control signal M6 controls the sixth selector switch 178 to sequentially selectively coupling second terminals of third components 32 to the reference voltage signal line V0 at a given time interval. A first output voltage from the first output voltage signal line Vout1 and a second output voltage from the second output voltage signal line Vout2 can be detected to determine a touch position and a touch pressure.

By comparing the time duration with time points at which the plurality of sensing units respectively receiving the control signals (e.g., the first control signal), a position of a sensing unit subject to touch can be determined. Because a respective one of the plurality of sensing units receives the first control signal at different time points in a given order, the comparison can effectively reveal the exact sensing unit that is subject to touch.

By comparing changes in voltage levels of the first output voltage and the third output voltage during the time duration with a plurality of first reference voltage levels and a plurality of third reference voltage levels respectively, a touch pressure can be determined with an enhanced accuracy. The plurality of reference voltage levels can be stored in a memory. Alternatively, a correlation function can be stored in a memory for determining the touch pressure. Optionally, the plurality of reference voltage levels or the correlation function can be stored in cloud or a remote server. Optionally, the plurality of reference voltage levels or the correlation function can be optimized based on a deep learning training unit.

The foregoing description of the embodiments of the invention has been presented for purposes of illustration and description. It is not intended to be exhaustive or to limit the invention to the precise form or to exemplary embodiments disclosed. Accordingly, the foregoing description should be retarded as illustrative rather than restrictive. Obviously, many modifications and variations will be apparent to practitioners skilled in this art. The embodiments are chosen and described in order to explain the principles of the invention and its best mode practical application, thereby to enable persons skilled in the art to understand the invention for various embodiments and with various modifications as are suited to the particular use or implementation contemplated. It is intended that the scope of the invention be defined by the claims appended hereto and their equivalents in which all terms are meant in their broadest reasonable sense unless otherwise indicated. Therefore, the term "the invention", "the present invention" or the like does not necessarily limit the claim scope to a specific embodiment, and the reference to exemplary embodiments of the invention does not imply a limitation on the invention, and no such limitation is to be inferred. The invention is limited only by the spirit and scope of the appended claims. Moreover, these claims may refer to use "first", "second", etc. following with noun or element. Such terms should be understood as a nomenclature and should not be construed as giving the limitation on the number of the elements modified by such nomenclature unless specific number has been given. Any advantages and benefits described may not apply to all embodiments of the invention. It should be appreciated that variations may be made in the embodiments described by persons skilled in the art without departing from the scope of the present invention as defined by the following claims. Moreover, no element and component in the present disclosure is intended to be dedicated to the public regardless of whether the element or component is explicitly recited in the following claims.

What is claimed is:

1. A sensing apparatus, comprising:
   a base substrate;
   a plurality of sensing units on the base substrate, a respective one of the plurality of sensing units comprising a first component and a second component;
   an elastic layer on a side of the plurality of sensing units distal to the base substrate and configured to undergo a deformation upon a touch;
   switches configured to, during a first period of the touch, control the first component to emit light, the second component to detect light reflected by a surface of the elastic layer, and output a first sensing signal, and, during a second period of the touch, control the second component to emit light, the first component to detect light reflected by the surface of the elastic layer, and output a second sensing signal;
   a processor configured to receive the first sensing signal and the second sensing signal, and determine a degree of the deformation of the elastic layer at each local position based on the first sensing signal and the second sensing signal;
   an input voltage signal line;
   a first output voltage signal line;
   a reference voltage signal line;
   a ground voltage signal line;
   a first selector switch configured to selectively couple a first terminal of the first component to one of the input voltage signal line or the first output voltage signal line;
   a second selector switch configured to selectively couple a second terminal of the first component to one of the reference voltage signal line or the ground voltage signal line;
   a third selector switch configured to selectively couple a first terminal of the second component to one of the input voltage signal line or the first output voltage signal line; and
   a fourth selector switch configured to selectively couple a second terminal of the second component to one of the reference voltage signal line or the ground voltage signal line.

2. The sensing apparatus of claim 1, further comprising a reflective layer on a side of the elastic layer distal to the base substrate, and configured to block light emitted from the first component or the second component from emitting out of the elastic layer.

3. The sensing apparatus of claim 1, further comprising:
   a memory configured to store a plurality of reference sensing signals corresponding to different degrees of deformation; and
   wherein the processor is configured to compare the first sensing signal and the second sensing signal with the plurality of reference sensing signals, and determine the degree of the deformation of the elastic layer at each local position based on a result of comparing.

4. The sensing apparatus of claim 1, wherein the respective one of the plurality of sensing units further comprises a third component;
   wherein the sensing apparatus further comprises a second output voltage signal line;
   a fifth selector switch configured to selectively couple a first terminal of the third component to one of the input voltage signal line or the second output voltage signal line; and
   a sixth selector switch configured to selectively couple a second terminal of the third component to one of the reference voltage signal line or the ground voltage signal line;
   wherein the third component is configured to detect light when a voltage level at the second terminal of the third component is higher than a voltage level at the first terminal of the third component to generate a photocurrent flowing from the second terminal of the third component to the first terminal of the third component.

5. The sensing apparatus of claim 1, wherein a total number of components in the respective one of the plurality of sensing units configured to emit light is one and a total number of components in the respective one of the plurality of sensing units configured to detect light is two.

6. The sensing apparatus of claim 1, wherein the first component is a light emitting diode and the second component is a photodiode.

7. The sensing apparatus of claim 1, wherein the first component is a photodiode and the second component is a photodiode.

8. The sensing apparatus of claim 1, wherein the elastic layer comprises an elastic resin material.

9. A sensing apparatus, comprising:
   a base substrate;
   a plurality of sensing units on the base substrate, a respective one of the plurality of sensing units comprising a first component and a second component;
   an elastic layer on a side of the plurality of sensing units distal to the base substrate and configured to undergo a deformation upon a touch;

switches configured to, during a first period of the touch, control the first component to emit light, the second component to detect light reflected by a surface of the elastic layer, and output a first sensing signal, and, during a second period of the touch, control the second component to emit light, the first component to detect light reflected by the surface of the elastic layer, and output a second sensing signal; and a processor configured to receive the first sensing signal and the second sensing signal, and determine a degree of the deformation of the elastic layer at each local position based on the first sensing signal and the second sensing signal;

wherein, during the first period of the touch, the switches are configured to control a voltage level at a first terminal of the first component to be higher than a voltage level at a second terminal of the first component to generate a first current flowing from the first terminal of the first component to the second terminal of the first component, thereby controlling the first component to emit light, and control a voltage level at a second terminal of the second component to be higher than a voltage level at a first terminal of the second component to generate a first photocurrent flowing from the second terminal of the second component to the first terminal of the second component, thereby controlling the second component to detect light reflected by the surface of the elastic layer and output a first sensing signal;

wherein, during the second period of the touch, the switches are configured to control a voltage level at the first terminal of the second component to be higher than a voltage level at the second terminal of the second component to generate a second current flowing from the first terminal of the second component to the second terminal of the second component, thereby controlling the second component to emit light, and control a voltage level at the second terminal of the first component to be higher than a voltage level at the first terminal of the first component to generate a second photocurrent flowing from the second terminal of the first component to the first terminal of the first component, thereby controlling the first component to detect light reflected by the surface of the elastic layer and output a second sensing signal.

10. An artificial skin, comprising:
a flexible base substrate;
a plurality of sensing units on the flexible base substrate, a respective one of the plurality of sensing units comprising a first component and a second component;
an elastic layer on a side of the plurality of sensing units distal to the flexible base substrate and configured to undergo a deformation upon a touch;
switches configured to, during a first period of the touch, control the first component to emit light, the second component to detect light reflected by a surface of the elastic layer, and output a first sensing signal, and, during a second period of the touch, control the second component to emit light, the first component to detect light reflected by the surface of the elastic layer, and output a second sensing signal;
a processor configured to receive the first sensing signal and the second sensing signal, and determine a degree of the deformation of the elastic layer at each local position based on the first sensing signal and the second sensing signal;
an input voltage signal line;
a first output voltage signal line;
a reference voltage signal line;
a ground voltage signal line;
a first selector switch configured to selectively couple a first terminal of the first component to one of the input voltage signal line or the first output voltage signal line;
a second selector switch configured to selectively couple a second terminal of the first component to one of the reference voltage signal line or the ground voltage signal line;
a third selector switch configured to selectively couple a first terminal of the second component to one of the input voltage signal line or the first output voltage signal line; and
a fourth selector switch configured to selectively couple a second terminal of the second component to one of the reference voltage signal line or the ground voltage signal line.

11. A method of detecting a touch, comprising:
during a first period of the touch, controlling a first component of a respective one of a plurality of sensing units to emit light, reflecting at least a portion of light emitted from the first component by a surface of an elastic layer, controlling a second component of the respective one of the plurality of sensing units to detect light reflected by the surface of the elastic layer, and outputting a first sensing signal;
during a second period of the touch, controlling the second component to emit light, reflecting at least a portion of light emitted from the second component by the surface of the elastic layer, controlling the first component to detect light reflected by the surface of the elastic layer, and output a second sensing signal;
processing the first sensing signal and the second sensing signal by a processor; and
determining degree of a deformation of the elastic layer at each local position based on the first sensing signal and the second sensing signal.

12. The method of claim 11, further comprising:
sequentially selectively coupling first terminals of first components of the plurality of sensing units to an input voltage signal line at a given time interval;
sequentially selectively coupling second terminals of first components of the plurality of sensing units to a ground voltage signal line at a given time interval;
sequentially selectively coupling first terminals of second components of the plurality of sensing units to a first output voltage signal line at a given time interval;
sequentially selectively coupling second terminals of second components of the plurality of sensing units to a reference voltage signal line at a given time interval; and
detecting a first output voltage from the first output voltage signal line thereby determining a touch position and a touch pressure.

13. The method of claim 11, further comprising:
during the first period of the touch, controlling a voltage level at a first terminal of the first component to be higher than a voltage level at a second terminal of the first component to generate a first current flowing from the first terminal of the first component to the second terminal of the first component, thereby controlling the first component to emit light, and controlling a voltage level at a second terminal of the second component to be higher than a voltage level at a first terminal of the second component to generate a first photocurrent flowing from the second terminal of the second component to the first terminal of the second component, thereby controlling the second component to detect light reflected by the surface of the elastic layer and output a first sensing signal;

during the second period of the touch, controlling a voltage level at the first terminal of the second component to be higher than a voltage level at the second terminal of the second component to generate a second current flowing from the first terminal of the second component to the second terminal of the second component, thereby controlling the second component to emit light, and controlling a voltage level at the second terminal of the first component to be higher than a voltage level at the first terminal of the first component to generate a second photocurrent flowing from the second terminal of the first component to the first terminal of the first component, thereby controlling the first component to detect light reflected by the surface of the elastic layer and output a second sensing signal.

14. The method of claim 11, further comprising:

sequentially selectively coupling first terminals of second components of the plurality of sensing units to an input voltage signal line at a given time interval;

sequentially selectively coupling second terminals of second components of the plurality of sensing units to a ground voltage signal line at a given time interval;

sequentially selectively coupling first terminals of first components of the plurality of sensing units to a first output voltage signal line at a given time interval;

sequentially selectively coupling second terminals of first components of the plurality of sensing units to a reference voltage signal line at a given time interval; and detecting a second output voltage from the first output voltage signal line thereby determining a touch position and a touch pressure.

15. The method of claim 11, further comprising:

further detecting light reflected by the surface of the elastic layer by a third component of the respective one of the plurality of sensing units; and outputting a third sensing signal from the third component of the respective one of the plurality of sensing units;

wherein an intensity of the third sensing signal is correlated to a degree of the deformation of the elastic layer at a local position.

16. The method of claim 15, further comprising:

sequentially selectively coupling first terminals of first components of the plurality of sensing units to an input voltage signal line at a given time interval;

sequentially selectively coupling second terminals of first components of the plurality of sensing units to a ground voltage signal line at a given time interval;

sequentially selectively coupling first terminals of second components of the plurality of sensing units to a first output voltage signal line at a given time interval;

sequentially selectively coupling second terminals of second components of the plurality of sensing units to a reference voltage signal line at a given time interval;

sequentially selectively coupling first terminals of third components of the plurality of sensing units to a second output voltage signal line at a given time interval;

sequentially selectively coupling second terminals of third components of the plurality of sensing units to the reference voltage signal line at a given time interval; and detecting a first output voltage from the first output voltage signal line and a second output voltage from the second output voltage signal line, thereby determining a touch position and a touch pressure.

* * * * *